United States Patent
Yang et al.

(10) Patent No.: US 11,434,277 B2
(45) Date of Patent: Sep. 6, 2022

(54) METHOD FOR HIGH-THROUGHPUT SCREENING OF NEUTRALIZING ANTIBODIES, NEUTRALIZING ANTIBODIES PRODUCED THEREFROM, AND USES THEREOF

(71) Applicant: ACADEMIA SINICA, Taipei (TW)

(72) Inventors: An-Suei Yang, Emeryville, CA (US); Ing-Chien Chen, Taipei (TW); Yi-Kai Chiu, Taipei (TW); Chung-Ming Yu, Taipei (TW); Cheng-Chung Lee, Taipei (TW); Chao-Ping Tung, Taipei (TW); Yueh-Liang Tsou, Taipei (TW); Yi-Jen Huang, Taipei (TW); Chia-Lung Lin, Taipei (TW); Hong-Sen Chen, Taipei (TW); Hwei-Jiung Wang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 207 days.

(21) Appl. No.: 16/757,460

(22) PCT Filed: Oct. 19, 2018

(86) PCT No.: PCT/US2018/056627
§ 371 (c)(1),
(2) Date: Apr. 20, 2020

(87) PCT Pub. No.: WO2019/079671
PCT Pub. Date: Apr. 25, 2019

(65) Prior Publication Data
US 2021/0070843 A1    Mar. 11, 2021

Related U.S. Application Data

(60) Provisional application No. 62/574,884, filed on Oct. 20, 2017.

(51) Int. Cl.
*C07K 16/00* (2006.01)
*C07K 16/10* (2006.01)

(52) U.S. Cl.
CPC ...... *C07K 16/1018* (2013.01); *C07K 2317/14* (2013.01); *C07K 2317/565* (2013.01); *C07K 2317/622* (2013.01); *C07K 2317/76* (2013.01)

(58) Field of Classification Search
CPC ............ C07K 16/1018; C07K 2317/14; C07K 2317/565; C07K 2317/622; C07K 2317/76
See application file for complete search history.

(56) References Cited

U.S. PATENT DOCUMENTS

2008/0014205 A1    1/2008  Horowitz et al.

FOREIGN PATENT DOCUMENTS

| TW | 201632547 A | | 9/2016 |
| WO | WO2016/137992 | * | 1/2016 |
| WO | WO2016/137992 A2 | | 9/2016 |

OTHER PUBLICATIONS

Ing-Chien Chen et al; "High throughput discovery of influenza virus neutralizing antibodies from phage-displayed synthetic antibody libraries."; published on Oct. 31, 2017, Scientific Reports 7, Article No. 14455; pp. 1-17.

Chao-Ping Tung; "Discovering neutralizing antibodies targeting the stem epitope of H1N1 influenza hemagglutinin with synthetic phage-displayed antibody libraries;" Scientific Reports | 5:15053 | DOI: 10.1038/srep15053; www.nature.com/scientificreports; Oct. 12, 2015. (pp. 16).

* cited by examiner

*Primary Examiner* — Lei Yao
(74) *Attorney, Agent, or Firm* — Muncy, Geissler, Olds & Lowe, P.C.

(57) ABSTRACT

Disclosed herein are methods for high-throughput screening of a virus-specific neutralizing antibody. According to certain embodiments of the present disclosure, the virus is an influenza virus. Also disclosed herein are the antibodies selected by the high-throughput screening method, and the uses thereof in the prophylaxis and/or treatment of viral infection.

2 Claims, 2 Drawing Sheets
Specification includes a Sequence Listing.

METHOD FOR HIGH-THROUGHPUT SCREENING OF NEUTRALIZING ANTIBODIES, NEUTRALIZING ANTIBODIES PRODUCED THEREFROM, AND USES THEREOF

CROSS-REFERENCE TO RELATED APPLICATION

This application is a U.S. National Stage Filing under 35 U.S.C. 371 from International Patent Application Serial No. PCT/US 18/56627, filed Oct. 19, 2018, and published on Apr. 25, 2019, which claims the priority of U.S. Ser. No. 62/574,884, filed Oct. 20, 2017, the disclosure of which are incorporated by reference herein in their entireties.

STATEMENT REGARDING PRIOR DISCLOSURES BY THE INVENTOR OR A JOINT INVENTOR UNDER 37 C.F.R. 1.77(B)(6)

Most of the subject matter of the invention described in the present application was published by the inventors, Ing-Chien Chen, Yi-Kai Chiu, Chung-Ming Yu, Cheng-Chung Lee, Chao-Ping Tung, Yueh-Liang Tsou, Yi-Jen Huang, Chia-Lung Lin, Hong-Sen Chen, Andrew H.-J. Wang, and An-Suei Yang in an article titled "High throughput discovery of influenza virus neutralizing antibodies from phage-displayed synthetic antibody libraries." The article was published on Oct. 31, 2017 on Scientific Reports 7, Article number: 14455 (2017). The publication was made by and/or originated from all member of the inventive entity of the present invention, and the entirety of this article is incorporated herein by reference. A copy of the article is provided in a concurrently filed Information Disclosure Statement pursuant to the guidance of 78 Fed. Reg. 11076 (Feb. 14, 2013).

BACKGROUND OF THE INVENTION

1. Field of the Invention

The present disclosure relates to a method of screening of neutralizing antibodies. More specifically, the present disclosure relates to a method of high-throughput screening of neutralizing antibodies against various viruses, including an influenza virus.

2. Description of Related Art

Yearly outbreaks of influenza virus infections lead to substantial social and economic burden worldwide. The economic burden due to influenza in the US alone in 2003 has been estimated to be about $87.1 billion. However, the loss of lives due to influenza dwarfs the economic burden: Global annual seasonal influenza attack rate, estimated by World Health Organization (WHO), has been 5-10% in adults and 20-30% in children, leading to 1 billion annual cases of influenza infection, 3-5 million annual cases of severe illness and 250,000-500,000 annual deaths, who are mostly high risk groups such as elderly, infants, and people with underlying chronical illness.

Pandemic influenza A virus (IAV) outbreaks pose much more severe challenges comparing with seasonal influenza epidemics. The pandemic influenza attack rates are much higher (over 50% attack rate in the 1918 flu pandemic) and young adult mortality rate between the ages of 20 and 40 years is particularly alarming, accounting for more than half of the deaths as in the 1918 flu pandemic. The pandemic outbreaks are particularly devastating because of the bourgeoning human population and interconnected traveling patterns. Three major influenza pandemics occur in the past century: 1918 H1N1 Spanish, 1957 H2N2 Asian, and 1968 H3N2 Hong Kong. The total deaths caused by these three major human influenza pandemics have been estimated to be 50-100 million worldwide, where the mortality rate for 1918 flu pandemic alone was 2%, causing 20-100 million deaths. The 21th century's first pandemic, unpredictedly caused by 2009 H1N1 influenza virus (Mexico) of swine origin, is reported by WHO of millions of cases and 16813 deaths (as of 2010 Mar. 19). While the next pandemic influenza outbreak has been unpredictable with our current knowledge, the concern over an avian strain of pandemic virus is certainly warranted, as revealed by the emergence of avian influenza strains, including H5N1 (Hong Kong) in 1997, H7N9 (China), H10N8 (China) and H6N1 (Taiwan) in 2013 and H5N6 (Hong Kong) in 2014, among which the highly pathogenic avian influenza H5N1 (Hong Kong) and H7N9 (China) are of particular concern. If virus genome reassortment or antigenic drift are to result in the new H7N9/H5N1 avian influenza virus transmissible among humans, a new pandemic could arise.

Countermeasure for IAV epidemics and pandemics have not provided enough protection to human population. Seasonal trivalent or quardrivalent influenza vaccines are conditionally effective, depending on the match of the predicted vaccine strains and the strains in circulation each year. More importantly, the majority of human population does not have protective immunity against pandemic influenza viruses and vaccines against the pandemic strains would be available with considerable delay of at least 5-6 months after the availability of the vaccine virus to vaccine manufacturers. By the time when the vaccine becomes available, substantial mortality, morbidity and economic loss could have already occurred. Universal vaccines with efficacy against a broad spectrum of influenza strains are still under development; even effective vaccines are available, there would be a delay of about 2 weeks before developing protective immunity. Stockpile of antiviral drugs (mostly neuraminidase inhibitors such as oseltamivir (Tamiflu)) as strategy for curbing influenza pandemics has been questioned. Moreover, influenza strains with pandemic threats could be resistant to current antivirals, as drug-resistant influenza virus strains have occurred due to antigenic shift and antigenic drift.

Passive immunotherapy with neutralizing antibodies to treat severe IAV infections can be a viable strategy in mitigating the threats of influenza epidemic and pandemic outbreaks. Human antibody discoveries based on culturing/ cloning human single memory and plasmablast B cells and displaying human antibody repertoires on phage particles have resulted in potent human neutralizing antibodies, many of which are broadly neutralizing antibodies (bnAbs) and are being tested for passive immunotherapy in human trials. However, affinity matured human antibodies with neutralizing efficacy against pandemic strains harboring genetic makeup unknown to human immune systems could be difficult to attain. Moreover, neutralization escape variants could eventually emerge due to the selection pressure of the widespread treatments with the neutralizing antibodies.

In view of the foregoing, there exists a need in the art for providing a method for high-throughput screening of neutralizing antibodies for use to respond to immediate threats of the emerging viral infections.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a method for high-throughput screening of a neutralizing antibody specific to a virus. The present method comprises the steps of, (a) providing a phage-displayed single-chain variable fragment (scFv) library that comprises a plurality of phage-displayed scFvs, wherein the heavy chain variable (VH) domain of each phage-displayed scFvs has a binding affinity to protein A, and the light chain variable (VL) domain of each phage-displayed scFvs has a binding affinity to protein L;

(b) exposing the phage-displayed scFv library of the step (a) to a viral antigen derived from the virus;

(c) selecting, from the phage-displayed scFv library of the step (b), a plurality of phages that express scFvs exhibiting binding affinity to the viral antigen under an acidic condition;

(d) respectively enabling the plurality of phages selected in the step (c) to express a plurality of soluble scFvs;

(e) exposing the plurality of soluble scFvs of the step (d) to the virus;

(f) determining the respective neutralizing efficacy of the plurality of soluble scFvs in the step (e); and (g) based on the results determined in the step (f), selecting one soluble scFv that exhibits superior efficacy over the other soluble scFvs of the plurality of soluble scFvs as the neutralizing antibody.

The virus may be an influenza virus, a measles virus, a coronavirus, a mumps virus, a marburg virus, an ebola virus, a rubella virus, a rhinovirus, a poliovirus, a hepatitis virus, a smallpox virus, a varicella-zoster virus, a severe acute respiratory syndrome virus, a retrovirus, a rotavirus, an adenoviruses, an adeno-associated virus or an alphavirus. According to some embodiments of the present disclosure, the virus is an influenza virus; in these embodiments, the viral antigen for selecting scFv in the steps (b) and (c) is preferably hemagglutinin (HA) or neuraminidase (NA).

According to some embodiments of the present disclosure, the step (c) is carried out by subjecting the product of the step (b) to a buffer having a pH value ranging between 2-6.8. According to one working example, the buffer has a pH value of 5.0.

Also disclosed herein is a neutralizing antibody produced by the present method. According to some embodiments, the VL domain of the neutralizing antibody has the amino acid sequence at least 85% identical to any of SEQ ID NOs: 1-28; and the VH domain of the neutralizing antibody has the amino acid sequence at least 85% identical to any of SEQ ID NOs: 29-56. According to specific example of the present disclosure, the VL domain of the neutralizing antibody has the amino acid sequence 100% identical to any of SEQ ID NOs: 1-28; and the VH domain of the neutralizing antibody has the amino acid sequence 100% identical to any of SEQ ID NOs: 29-56.

Another aspect of the present disclosure pertains to a method of producing a recombinant antibody. The method comprises the steps of, (a) selecting a neutralizing antibody by use of the present high-throughput screening method;

(b) extracting a phagemid DNA corresponding to the phage that expresses the neutralizing antibody of the step (a);

(c) respectively amplifying a first nucleic acid sequence that encodes a VL domain, and a second nucleic acid sequence that encodes a VH domain by PCR using the phagemid DNA of the step (b) as a template;

(d) inserting the first and second nucleic acid sequences into an expression vector that comprises a third and a fourth nucleic acid sequences, wherein the third nucleic acid sequence encodes the light chain constant (CL) domain of an immunoglobulin, and the fourth nucleic acid sequence encodes the heavy chain constant (CH) domain of the immunoglobulin; and (e) transfecting a host cell with the expression vector of the step (d) that comprises the first, second, third, and fourth nucleic acid sequences so as to produce the recombinant antibody.

According to the embodiments of the present disclosure, the first nucleic acid sequence is disposed at the upstream of the third nucleic acid sequence, and the second nucleic acid sequence is disposed at the upstream of the fourth nucleic acid sequence. Preferably, the immunoglobulin is immunoglobulin G (IgG).

According to certain embodiments, the host cell of the step (e) is a mammalian cell.

The thus-produced recombinant antibody comprises a VL domain, a CL domain, a VH domain and a CH domain. According to some embodiments, the VL domain of the recombinant antibody has the amino acid sequence at least 85% identical to any of SEQ ID NOs: 1-28; and the VH domain of the recombinant antibody has the amino acid sequence at least 85% identical to any of SEQ ID NOs: 29-56. According to specific example of the present disclosure, the VL domain of the recombinant antibody has the amino acid sequence 100% identical to any of SEQ ID NOs: 1-28; and the VH domain of the recombinant antibody has the amino acid sequence 100% identical to any of SEQ ID NOs: 29-56.

Another aspect of the present disclosure is directed to a method of treating or preventing a virus infection in a subject in need thereof. The method comprises administering to the subject an effective amount of the present neutralizing antibody or the present recombinant antibody.

The subject treatable with the present method is a mammal; preferably, the subject is a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings. A brief description of the drawings is summarized below.

FIGS. 1A and 1C: 15 GH2 phage-displayed scFv libraries are selected for HA binding. The y-axis shows the ratio of the output/input titer of the phage library in each of the biopanning rounds (x-axis). FIGS. 1B and 1D: The polyclonal soluble scFvs secreted in the *E. coli* culture media of the output phage libraries are assayed for HA trimer binding with ELISA (y-axis) for the biopanning rounds (x-axis) with each of the 15 phage-displayed scFv libraries. The experiments are repeated twice, as shown in the panels. Experimental details are described in Methods.

DESCRIPTION

Figure 1A:
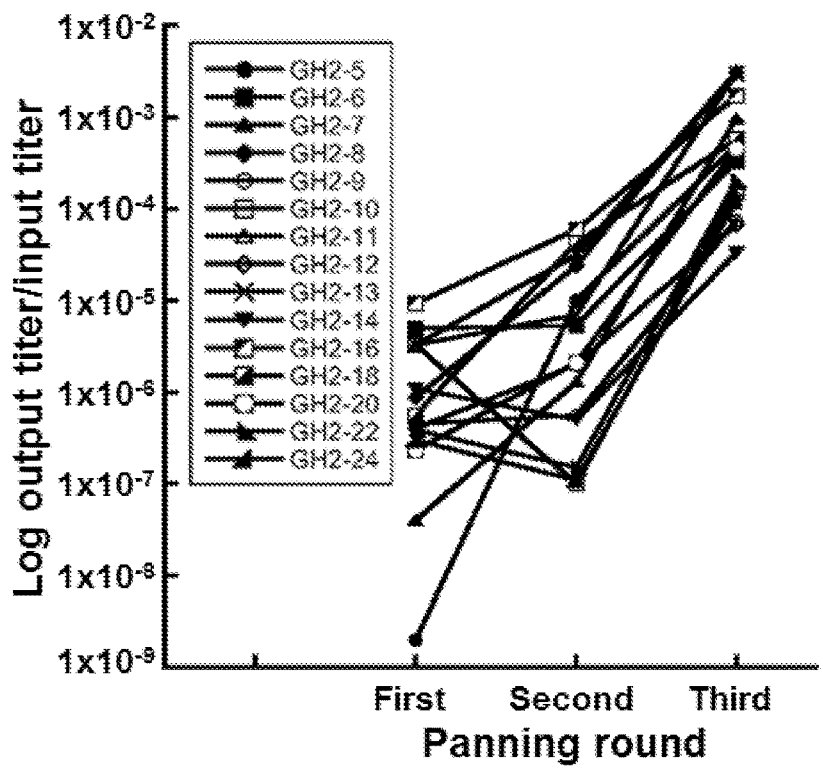
FIGS. 1A to 1D are results respectively depicting the biopanning of the synthetic antibody libraries against immobilized HA trimer of H1N1 CA/09, in which the biopanning was performed by washing phase of pH 5.0 (FIGS. 1A and 1B) or pH 7.4 (FIGS. 1C and 1D).

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, and Glyco can serve as an antigen. Furthermore, antigens can be derived from recombinant or genomic DNA. A skilled artisan will understand that any DNA, which comprises a nucleic acid sequence or a partial nucleic acid sequence encoding a protein that elicits an immune response, therefore encodes an "antigen" as that term is used herein. Furthermore, one skilled in the art will understand that an antigen needs not be encoded solely by a full length nucleic acid sequence of a gene; it can also be encoded by partial nucleic acid sequences of more than one gene and that these nucleic acid sequences are arranged in various combinations to elicit the desired immune response. Moreover, a skilled artisan will understand that an antigen needs not to be encoded by a "gene" at all; it is readily apparent that an antigen can be synthesized or can be derived from a biological sample. Such a biological sample can include, but is not limited to, a tissue sample, a tumor sample, a cell, or a biological fluid.

The term "antibody" is used in the broadest sense and specifically covers monoclonal antibodies (including full length monoclonal antibodies), polyclonal antibodies, multi-specific or multivalent antibodies (e.g., bi-specific antibodies), and antibody fragments so long as they exhibit the desired biological activity. "Antibody fragments" comprise a portion of a full-length antibody, generally the antigen binding or variable region thereof. Examples of antibody fragments include fragment antigen-binding (Fab), Fab', F(ab')2, single-chain variable fragment (scFv), diabodies, linear antibodies, single-chain antibody molecules, and multi-specific antibodies formed from antibody fragments.

The term "antibody library" refers to a collection of antibodies and/or antibody fragments displayed for screening and/or combination into full antibodies. The antibodies and/or antibody fragments may be displayed on a ribosome; on a phage; or on a cell surface, in particular a yeast cell surface.

As used herein, the term "single-chain variable fragment" or "scFv" is a fusion protein comprising the variable regions of the heavy (VH) and light chains (VL) of an immunoglobulin, in which the VH and VL are covalently linked to form a VH:VL heterodimer. The VH and VL are either joined directly or joined by a peptide-encoding linker, which connects the N-terminus of the VH with the C-terminus of the VL, or the C-terminus of the VH with the N-terminus of the VL. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including VH- and VL-encoding sequences.

The term "$EC_{50}$," as used herein, refers to the concentration of an antibody or an antigen-binding portion thereof, which induces a response, either in an in vitro or an in vivo assay, which is 50% of the maximal response, i.e., halfway between the maximal response and the baseline.

The term "phagemid" refers to a vector, which combines attributes of a bacteriophage and a plasmid. A bacteriophage is defined as any one of a number of viruses that infect bacteria.

"Percentage (%) sequence identity" with respect to any amino acid sequence identified herein is defined as the percentage of amino acid residues in a candidate sequence that are identical with the amino acid residues in the specific reference sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNAS-TAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage sequence identity of a given sequence A to a subject sequence B (which can alternatively be phrased as a given sequence A that has a certain % sequence identity to a given sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in the subject sequence B.

As discussed herein, minor variations in the amino acid sequences of antibodies are contemplated as being encompassed by the presently disclosed and claimed inventive concept(s), providing that the variations in the amino acid sequence maintain at least 85% sequence identity, such as at least 85%, 86%, 87%, 88%, 89%, 90%, 91%, 92%, 93%, 94%, 95%, 96%, 97%, 98% and 99% sequence identity. Antibodies of the present disclosure may be modified specifically to alter a feature of the peptide unrelated to its physiological activity. For example, certain amino acids can be changed and/or deleted without affecting the physiological activity of the antibody in this study (i.e., its ability to neutralizing influenza virus). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of antibodies can be readily prepared by those of ordinary skill in the art. Preferred amino- and carboxy-termini of fragments or analogs occur near boundaries of functional domains.

The term "subject" refers to a mammal including the human species that is treatable with methods of the present invention. The term "subject" is intended to refer to both the male and female gender unless one gender is specifically indicated.

II. Description of the Invention

The present disclosure is directed to a high-throughput screening method for identifying a neutralizing antibody against a virus. The method comprises the steps of, (a) providing a phage-displayed scFv library that comprises a plurality of phage-displayed scFvs, wherein the VH domain of each phage-displayed scFvs has a binding affinity to protein A, and the VL domain of each phage-displayed scFvs has a binding affinity to protein L;

(b) exposing the phage-displayed scFv library of the step (a) to a viral antigen derived from the virus;

(c) selecting, from the phage-displayed scFv library of the step (b), a plurality of phages that express scFvs exhibiting binding affinity to the viral antigen under an acidic condition;

(d) respectively enabling the plurality of phages selected in the step (c) to express a plurality of soluble scFvs;

(e) exposing the plurality of soluble scFvs of the step (d) to the virus;

(f) determining the respective neutralizing efficacy of the plurality of soluble scFvs in the step (e); and (g) based on the results determined in the step (f), selecting one soluble scFv that exhibit superior efficacy over the other soluble scFvs of the plurality of soluble scFvs as the neutralizing antibody.

In general, the present method is useful in screening a neutralizing antibody specific to/against a virus that enters a cell through endocytosis. Non-limiting examples of such virus include, influenza virus (e.g., influenza A virus (IAV)), measles virus, coronavirus, mumps virus, marburg virus, ebola virus, rubella virus, rhinovirus, poliovirus, hepatitis virus (e.g., hepatitis A virus (HAV), hepatitis B virus (HBV) and hepatitis C virus (HCV)), smallpox virus, varicella-zoster virus, severe acute respiratory syndrome virus, retrovirus (e.g., lentivirus), rotavirus, adenoviruses, adeno-associated virus or alphavirus. According to some embodiments of the present disclosure, the virus is IAV, which may be any of H1N1, H2N2, H3N2, H5N1, H7N7, H1N2, H9N2, H7N2, H7N3, H10N7 or H7N9. In one working example, the virus is H1N1.

In the step (a), a phage-displayed scFv library is provided. According to the embodiments of the present disclosure, the framework of the phage-displayed scFv library is based on the human IGKVI-NL1*01/IGHV3-23*04 germline sequence, and the complementarity determining region (CDR, including CDR-L1, CDR-L2, CDR-L3, CDR-H1, CDR-H2, and CDR-H3) thereof rare diversified by PCR reaction using desired primers. After the selection of protein A and protein L, the phage-displayed scFv library (hereinafter as "GH2 library," including GH2-5, GH2-6, GH2-7, GH2-8, GH2-9, GH2-10, GH2-11, GH2-12, GH2-13, GH2-14, GH2-16, GH2-18, GH2-20, GH2-22, and GH2-24 libraries as illustrated in the examples of the present disclosure) is produced, in which each of the plurality of phage-displayed scFvs has a VH domain capable of binding to protein A, and a VL domain capable of binding to protein L. This phage-displayed scFv library can be constructed using the method described in the co-pending PCT application, PCT/US2016/19128 and the publication of Ing-Chien Chen et al. (High throughput discovery of influenza virus neutralizing antibodies from phage-displayed synthetic antibody libraries, *Scientific Reports* 7, Article number: 14455 (2017)). The entirety of the application and publication are incorporated herein by reference.

In the step (b), the GH2 library is exposed to a viral antigen derived from the virus. For example, in the case when the virus is HBV, the viral antigen may be the surface antigen of HBV (HBsAg). Alternatively, in the case when the virus is coronavirus, then the viral antigen may be the spike (S) or the envelope (E) protein. According to certain embodiments of the present disclosure, the virus is IAV, and the viral antigen may be hemagglutinin (HA) or neuraminidase (NA). According to one embodiment, the viral antigen HA, which is immobilized on a matrix (such as an agarose resin or polyacrylamide) and then mixed with the present GH2 library.

In the step (c), a plurality of phages respectively expressing scFvs that exhibit binding affinity to the viral antigen are selected from the GH2 library. Specifically, the product of the step (b) is subject to an acidic treatment (for example, a washing buffer having a pH value ranging between 2-7, such as 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9 or 7; preferably, a buffer having a pH value of 5.0) that mimics the condition of the viral entry process. The acidic treatment ensures that the selected scFvs are capable of binding to the virus during the membrane fusion process (which occurs between the viral membrane and the endosomal membrane of the host cells), and thus, blocking the viral entry into the host cells. After the acidic treatment, the phages that express scFvs exhibiting binding affinity to the viral antigen are then treated with an elution buffer (such as, a glycine solution, pH 2.2) so as to disrupt the binding between the viral antigen and phage-display scFv. By this way, a plurality of phages that express scFvs specific for the viral antigen are collected.

Next, in the step (d), the plurality of phages selected in the step (c) are subject to conditions that enable them to produce a plurality of soluble scFvs. This step can be carried out by using methods known to any person having ordinary skill in the art. According to certain embodiments of the present disclosure, the expression of VH and VL domains may be driven by a lactose operon (lac operon); as known by one skilled artisan, the lac operon would be induced by isopropyl-thio-β-D-galactoside (IPTG), which then drives the expression of the down-stream genes (i.e., genes encoding the VH and VL domains). The produced scFv are then secreted into the supernatant of culture medium and could be collected therefrom.

In the step (e), the soluble scFvs produced in the step (d) are respectively mixed with the virus so as to form the virus-scFv complexes.

Then, in the step (f), the neutralizing efficacy of each of the soluble scFvs is determined. Specifically, the virus-scFv complexes formed in the step (e) are respectively added to a virus-permissive cell (e.g., the MDCK cell for IAV infection) and incubated for a period of time (e.g., 24 hours). Then, the viral activity (e.g., the viral expression or replication) in the virus-permissive cell is assessed by a method known to any persons having ordinary skill in is the art; for example, enzyme-linked immunosorbent assay (ELISA). In general, the neutralizing efficacy is inversely proportional to the viral activity; in other words, the higher the neutralizing efficacy, the lower the viral activity.

Alternatively, the neutralizing efficacy may be determined by measuring the respective cell viability of the virus-permissive cells treated with the virus-scFv complexes. However, the present disclosure is not limited thereto.

Finally, in the step (g), the neutralizing antibody is selected based on the neutralizing efficacy determined in the step (f). More specifically, the soluble scFv that exhibits superior efficacy over the other soluble scFvs of the plurality of soluble scFvs is selected as the neutralizing antibody.

The present high-throughput screening method is advantageous at least in that it eliminates the labor-intensive and time-consuming process in the preparation of virus-specific antibody. Consequently, the throughput rate in discovering and optimizing the neutralizing antibodies is substantially improved.

The selected neutralizing antibody is useful in the preparation of a recombinant antibody, which structurally comprises a VL domain, a CL domain, a VH domain and a heavy chain constant (CH) domain. The method of using the neutralizing antibody to produce the recombinant antibody comprises the steps of, (a) providing a phage that expresses the neutralizing antibody;

(b) extracting the phagemid DNA corresponding to the phage of the step (a);

(c) respectively amplifying a first nucleic acid sequence that encodes a VL domain, and a second nucleic acid sequence that encodes a VH domain by PCR using the phagemid DNA of the step (b) as a template;

(d) inserting the first and second nucleic acid sequences into an expression vector that comprises a third and a fourth nucleic acid sequences, wherein the third nucleic acid sequence encodes the light chain constant (CL) domain of an immunoglobulin, and the fourth nucleic acid sequence encodes the heavy chain constant (CH) domain of the immunoglobulin; and (e) transfecting a host cell with the expression vector of the step (d) that comprises the first, second, third, and fourth nucleic acid sequences so as to produce the recombinant antibody.

In the present method, the phage that expresses the neutralizing antibody against the virus is used as a starting material for the preparation of a recombinant antibody (i.e., step (a)).

Then, the phagemid DNA corresponding to the antibody-expressing phage is extracted as described in step (b). Depending on intended purposes, the phagemid may be extracted by lysing the phage; alternatively, the phagemid may be obtained from a bacterial clone (i.e., the phagemid-containing bacterial clone). The extraction of phage DNA from the phage or bacterial clone could be achieved via any conventional DNA extraction technique; for example, the phenol/chloroform assay, and detergent (e.g., sodium dodecyl sulfate, Tween-20, NP-40, and Triton X-100)/acetic acid assay.

In the step (c), the thus extracted phagemid DNA then serves as a template to respectively amplify the first nucleic acid sequence that encodes the CDR-H1, CDR-H2, and CDR-H3 by PCR using specific primers

```
(forward primer: CGTGTCGCATCTGAAGTGCA
GCTGGTGGAATCGGGA, SEQ ID NO: 57;
reverse primer: GACCGATGGGCCCTTGGTGCT
AGCCGAGCTCACGGTAACAAGGGTGCC,
SEQ ID NO: 58),
```

58), and the second nucleic acid sequence that encodes the CDR-L1, CDR-L2, and CDR-L3 by PCR using specific primers

```
(forward primer: CAGGTGCACGATGTGATGGTACCGATATTC
AAATGACCCAGAGCCCGAGCAGCCTGAGC, SEQ ID NO: 59;
reverse primer: TGCAGCCACCGTACGTTTGATTTCCACCTTG
GTGCC, SEQ ID NO: 60).
```

In the step (d), the amplified first and second nucleic acid sequences are inserted into an expression vector, which comprises a third nucleic acid sequence encoding the constant regions of the heavy chain of an immunoglobulin, and a fourth nucleic acid sequence encoding the constant regions of the light chain of the immunoglobulin. As could be appreciated, the immunoglobulin can be any of IgG, IgA, IgD, IgE, and IgM. In one preferred embodiment of the present disclosure, the immunoglobulin is IgG. Specifically, the first and second nucleic acid sequences are first linked by a linker, which is amplified from pIgG vector by PCR. According to the embodiment of the present disclosure, the linker comprises in sequence: the CL domain, a bovine growth hormone (BGH) polyadenylation (polyA) signal, a human CMV promoter, and a signal peptide of IgG heavy chain. For the presences of the complementary sequences between the 3'-end of second nucleic acid sequence and the 5'-end of linker, and the complementary sequences between the 3'-end of the linker and the 5'-end of the first nucleic acid sequence, the second nucleic acid sequence, the linker and the first nucleic acid sequence can be assembled in sequence via overlap extension polymerase chain reaction (OE-PCR). The assembled product is then inserted into the expression vector pIgG by use of the restriction enzymes. Structurally, the constructed expression vector comprises in sequence: a first human CMV promoter, a signal peptide of IgG light chain, the second nucleic acid sequence, the CL domain, a first BGH-polyA signal, a second human CMV promoter, a signal peptide of IgG heavy chain, the first nucleic acid sequence, the CH domain, and a second BGH-polyA signal, in which the second nucleic acid sequence and the CL domain are driven by the first human CMV promoter so as to express the light chain of the recombinant antibody, and the first nucleic acid sequence and the CH domain are driven by the second human CMV promoter to express the heavy chain of the recombinant antibody.

In step (e), the expression vector constructed in step (d) is transfected into a host cell so as to produce the present recombinant antibody. The commonly used host cell is a mammalian cell, such as a HEK293 cell. The transfection can be performed by any method familiar by one skilled artisan, including chemical-based method (e.g., calcium phosphate, liposome, and cationic polymer), non-chemical method (e.g., electroporation, cell squeezing, sonoporation, optical transfection, protoplast fusion, and hydrodynamic delivery), particle-based method (e.g. gene gun, magnetofection, and impalefection), and viral method (e.g., adenoviral vector, sindbis viral vector, and lentiviral vector). The thus produced recombinant antibody is secreted into the supernatant of the culture medium, and can be purified therefrom by any purification method familiar by any skilled person; for example, the purification can be achieved by affinity binding with protein A or protein G.

According to certain embodiments of the present disclosure, the VL domain of the present neutralizing antibody or the present recombinant antibody has the amino acid sequence at least 85% (e.g., 85%, 86%, 87%, 88%, 89%, 90%, 91%, 92%, 93%, 94%, 95%, 96%, 97%, 98%, 99% or 100%) identical to any of SEQ ID NOs: 1-28; and the VH domain of the present neutralizing antibody or the present recombinant antibody has the amino acid sequence at least 85% (e.g., 85%, 86%, 87%, 88%, 89%, 90%, 91%, 92%, 93%, 94%, 95%, 96%, 97%, 98%, 99% or 100%) identical to any of SEQ ID NOs: 29-56. According to one working example of the present disclosure, the VL domain of the present neutralizing antibody or the present recombinant antibody has the amino acid sequence 100% identical to any of SEQ ID NOs: 1-28; and the VH domain of the present neutralizing antibody or the present recombinant antibody has the amino acid sequence 100% identical to any of SEQ ID NOs: 29-56. As would be appreciated, the sequence (e.g., the framework sequence) of the VL and VH domains may vary (e.g., being substituted by conserved or non-conserved amino acid residues) without affecting the binding affinity and/or specificity of the present antibody. Preferably, the sequence(s) of the VL and VH domains is/are conservatively substituted by one or more suitable amino acid(s) with similar properties; for example, the substitution of leucine (an nonpolar amino acid residue) by isoleucine, alanine, valine, proline, phenylalanine, or tryptophan (another nonpolar amino acid residue); the substitution of aspartate (an acidic amino acid residue) by glutamate (another acidic amino acid residue); or the substitution of lysine (an basic amino acid residue) by arginine or histidine (another basic amino acid residue).

Also included herein are the uses of the present neutralizing antibody or recombinant antibody for the preparation of a medicament or a pharmaceutical composition for treating or preventing a virus infection. The medicament or pharmaceutical composition comprises an effective amount of the present neutralizing antibody or recombinant antibody, and optionally, a pharmaceutical acceptable carrier.

Another aspect of the present disclosure is directed a method of treating or preventing a virus infection in a subject in need thereof; the method comprises administering to the subject an effective amount of the present neutralizing antibody, recombinant antibody, medicament or pharmaceutical composition.

The subject treatable with the present method is a mammal; for example, a mouse, a rat, a pig, a monkey, a rabbit, a dog and a cat. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the an can, based on the description herein, utilize the present invention to its fullest extent.

EXAMPLE

Materials and Methods
Cell Lines

The microneutralization ability and $IC_{50}$ were determined by MDCK (Madin-Darby canine kidney, ATCC CCL-34) epithelial cells, which were cultured in MEM medium supplemented with NEAA (non-essential amino acids), 2 mM L-glutamine, and 10% fetal bovine serum at 37° C. in a 5% $CO_2$ humidified atmosphere incubator. 293T cells (ATCC CRL-3216) were cultured in DMEM medium supplemented with 10% fetal bovine serum (FBS), penicillin-streptomycin (100X). Suspension HEK293 cells were cultured in serum free 293 expression medium at 37° C. with shaking 110 rpm in 8% $CO_2$ incubator.

Virus

H1N1 CA/09 influenza A virus, a recombinant virus NYMC X-181, was supplied by Taiwan's CDC. Embryonic eggs (10-day-old) were used to propagate virus stock. H1N1 CA/09 influenza A virus (1000 $TCID_{50}$) was injected into allantoic cavity to amplify virus. After incubation for 60 hours, the virus solution was harvested, concentrated by ultracentrifugation (25000×g for 2 hours) and resuspended in PBS.

$TCID_{50}$

The $TCID_{50}$ (50% tissue culture infectious dose) of H1N1 CA/09 influenza virus titer was determined in MDCK cells with a few modification. Briefly, the virus was 10-fold serially diluted in infection buffer (MEM/NEAA medium supplied with 0.3% BSA). PBS-washed MDCK cells ($3 \times 10^4$ cells per well in a 96-well plate) were infected by the diluted virus solutions for 1 hour and then washed with PBS twice to remove virus solution. Survival MDCK cells were fixed with ice-cold methanol-acetone (1:1 (v/v)) and stained with 0.5% crystal violet 3 days post-infection. Each dilution was performed 8 replicates and the $TCID_{50}$ was calculated.

Expression and Purification of Hemagglutinin (HA) Trimer

The cDNAs corresponding to residues 11-329 (HA1) and 1-176 (HA2), based on H3 numbering, of the ectodomain of the H1N1 CA/09, H5N1 VN/04, H3N2 WN/05, and H7N9 AH/13 hemagglutinin (HA) from A/California/07/2009 (H1N1; Accession No. ACP41953.1), A/Vietnam/1203/2004 (H5N1; Accession No. AY651334), A/Wisconsin/67/2005 (H3N2; Accession No. AFH00648.1), and A/Anhui/1-BAL-F_RG17/2013 (H7N9, Accession No. AHZ59831.1), respectively, were codon-optimized for eukaryotic cell expression and fused to an N-terminal gp67 signal peptide (MLL-VNQSHQGFNKEHTSKMVSAIVLYVLLAAAAHSAFA, SEQ ID NO: 61) and to a C-terminal thrombin cutting site, trimerization domain and 6-His-tag (ASLVPRGSPGSGYIPEAPRDGQAYVRKDGEWVLL-STFLGHHHHHH, SEQ ID NO: 62) by PCR. These HA expression cassettes were inserted into pFastBac-1, a baculoviral transfer vector. HA protein was produced by infecting suspension cultures of SF9 cells ($3 \times 10^6$ cells/mL) (ATCC CRL-1711) with recombinant baculovirus at an MOI of 5 and incubated at 27° C. with shaking at 110 rpm for 72 hours. The cultures were clarified by two rounds of centrifugation (1000×g and 12000×g for 30 minutes, 4° C., respectively). The supernatants containing HA was filtered by 0.8 μm pore size filter before purification. The HA was purified by $Ni^{2+}$-covalent bound column by gradient from 10 mM to 500 mM imidazole in TS solution (Tris-HCl 20 mM, NaCl 50 mM, pH 8.0). The fractions containing HA were introduced to column chromatography and eluted by gradient from 50 mM to 1000 mM NaCl in Tris-HCl 20 mM, pH 8.0. The fractions containing HA were concentrated and subjected to size exclusion chromatography with TS solution. The fractions containing HA were collected and stored in 4° C. or −80° C. For crystallization, the HA were digested with thrombin (0.2 unit per mg HA at 4° C. overnight) to remove the trimerization domain and 6-His-tag. The digested materials were purified by the size exclusion column with TS solution directly. The purified monomeric HA were mixed with 1.5 molar ratio of S40 Fab at 4° C. overnight with gently shaking. The HA-Fab complex was purified by the size exclusion column with TS solution to remove excess Fab.

Establishment of Phage-Displayed scFv Library 15 phage-displayed scFv libraries were established in the invention. The framework of these phage-displayed scFv libraries was based on the human IGKV1-NL1*01/IGHV3-23*04 germline sequence, in which the CDR-L1, CDR-L2, CDR-L3, CDR-H1, CDR-H2 and CDR-H3 sequences were respectively diversified as described in the co-pending PCT application, PCT/US2016/19128 and the publication of Ing-Chien Chen et al. (High throughput discovery of influenza virus neutralizing antibodies from phage-displayed synthetic antibody libraries, *Scientific Reports* 7, Article number: 14455 (2017)).

The thus-produced phage-displayed libraries were respectively designated as GH2-5, GH2-6, GH2-7, GH2-8, GH2-9, GH2-10, GH2-11, GH2-12, GH2-13, GH2-14, GH2-16, GH2-18, GH2-20, GH2-22, and GH2-24 libraries, in which each of the libraries has been constructed with complexity of more than $10^9$.

Selection and Screening of Anti-HA Monoclonal scFvs from Phage-Displayed scFv Libraries (1) Phage Display Selection-Amplification Cycles Recombinant H1N1 CA/09 HA (10 μg per well) was coated on 96-well immunoplates, and then blocked with 5% skim milk in PBST (1× PBS containing 0.05% (v/v) Tween 20, pH 7.4) for 1 hour. After blocking, 100 μL of resuspended polyethylene glycol/NaCl-precipitated phage library ($10^{13}$ cfu/mL in blocking buffer) was added to each well for 1 hour under gently shaking. The plate was then washed with PBST and PBS for three rounds. Specifically, in the biopanning with acidic washing phase, the plate was washed with (1) 200 μL PBST (pH 7.4) for 12 times and 200 μL PBS (pH 7.4) for times in the first round of biopanning; (2) 200 μL PBST (pH 5.0) for 12 times and 200 μL PBS (pH 7.4) for 2 times in the second round of biopanning; and (3) 200 μL PBST (pH 5.0) for 12 times and 200 μL PBS (pH 7.4) for 2 times in the third round of biopanning. In the control group (i.e., the biopanning with neutral washing phase), the plate was washed with (1) 200 μL PBST (pH 7.4) for 12 times and 200 μL PBS (pH 7.4) for 2 times in the first round of biopanning; (2) 200 μL PBST (pH 7.4) for 12 times and 200 μL PBS (pH 7.4) for 2 times in the second round of biopanning; and (3) 200 μL PBST (pH 7.4) for 12 times and 200 μL PBS (pH 7.4) for 2 times in the third round of biopanning.

After the washing steps, the bound phages were eluted with 100 μL of 0.1 M HCl/glycine (pH 2.2) per well, and immediately neutralized with 8 μL of 2 M Tris-base buffer (pH 9.1). The eluted phages were mixed with 1 mL of *E. coil* ($A_{600\ nm}$=0.6) for 30 minutes at 37° C.; uninfected bacteria were eliminated by adding ampicillin. After the ampicillin treatment for 30 minutes, the bacterial culture was infected with 100 μL M13KO7 helper phage (about $10^{11}$ CFU total) at 37° C. for 1 hour, and then added to 50 mL of 2X YT medium containing kanamycin 50 μg/mL and ampicillin 100 μg/mL overnight at 37° C. with vigorously shaking. The rescued phage library was precipitated with 20% polyethylene glycol/NaCl, and resuspended in PBS. The concentrated phage solution was used for the next round of panning.

(2) Ratio of Output/Input Phage Library Titer

In each biopanning procedure as described above, the output (eluted) and input phage were tittered with fresh-prepared E. coil, and the ratio of output/input titer was calculated.

(3) Polyclonal Soluble scFvs in E. coli Culture Media Evaluated for Antigen Binding with ELISA 50 μL rescued phage from each cycle of biopanning above was mixed with 750 μL of E. coil ($A_{600\ nm}$=0.6) in 96-well deep well culture plate and incubated at 37° C. with vigorously shaking. One hour later, 100 μL ampicillin was added to final concentration 100 μg/mL ampicillin. 100 μL of 10 mM IPTG was added to each well (final concentration 1 mM) after $A_{600\ nm}$>1.0, and the plate was incubated at 37° C. with vigorously shaking overnight. The plate was centrifuged at 3000×g for 10 minutes and the supernatants were used for ELISA binding assay.

(4) ELISA Assay for Soluble scFv-Antigen Binding

After 2-3 rounds of selection-amplification cycle, single colonies were picked and soluble monoclonal scFvs secreted in the E. coli cultures were prepared. 96-well immunoplate coated with CA/09 H1 HA 0.5 μg per well was blocked with 5% skim milk in PBST for 1 hour. 100 μL cultured medium with secreted scFv was added to the plate for binding. After 1 hour of binding and washing six times with PBST, 100 μL anti E-tag-HRP (1:4000 dilution) was added to each well. After 1 hour incubation, the plate was washed six times with PBST buffer and twice with PBS, developed for 3 minutes with 3,3',5,5'-tetramethyl-benzidine peroxidase substrate (TMB substrate), quenched with 1.0 M HCl and read spectrophotometrically at 450 nm.

(5) ELISA Assay for Soluble scFv Folding with Protein L/Protein A

In additional to test the antigen binding of secreted scFv, well-folded scFvs were identified with protein L and protein A binding. 96-well immunoplate coated with protein L (0.1 μg per well) was blocked and added with scFv cultured medium as described above. The signals were developed with protein A conjugated with horseradish peroxidase (1:5000 dilution).

Microneutralization Assay

MDCK cells (3×10⁴ cells/well) were seeded in 96-well plates for 16 hours and washed twice with PBS prior to be infected by virus-scFv mixture. Filtrated scFv solution was freshly mixed with 100 $TCID_{50}$ viral solution (1:1 (v/v)) and incubated for 1 hour at 37° C. Virus-scFv mixtures were then added to infect PBS-washed MDCK cells for another 1 hour at 37° C. Virus-scFv mixtures were removed and cells were washed twice with PBS after absorption. Infected MDCK cells were cultured in infection buffer 24 hours post-infection and then fixed with methanol-acetone (1:1 (v/v)). After fixation, MDCK cells were treated with 0.5% TRITON X-100 in PBS for 5 minutes, and then with blocking buffer for 1 hour. The mouse anti-influenza A viral nucleoprotein IgG antibody (1:2000 dilution) was used for detection of viral nucleoprotein production with goat anti-mouse antibody-HRP (1:1000 dilution) and TMB peroxidase substrate. Each filtrated scFv was assayed once in a 96-well plate with duplicate and every test was performed with two independent experiments. The relative viral activity was calculated with ELISA readings, in which the ELISA readings of virus-only control and that of negative control (no virus and no scFv) were set as 100% and 0% respectively. The neutralization percentage was calculated by the reduction of virus infection due to scFv addition.

$IC_{50}$ Determination

MDCK cells were used to determine the half of maximal inhibitory concentration ($IC_{50}$) of purified IgG candidates. In brief, a serial 2-fold diluted IgG was mixed with 100 $TCID_{50}$ viral solution and incubated for 1 hour at 37° C. PBS-washed cells were infected by virus-IgG solution for another 1 hour at 37° C. After fixation with methanol-acetone (1:1 (v/v)), MDCK cells were treated with 0.5% TRITON X-100 in PBS and then blocking buffer. Mouse anti-influenza A viral nucleoprotein IgG antibody (1:2000 dilution) and goat anti-mouse antibody conjugated with HRP (1:1000 dilution) were used to detect propagated viruses. TMB substrate (100 μL per well) was added and the absorbance at 450 nm was measured after reactions were stopped by adding 1N HCl (100 μL per well). Each concentration of diluted IgG was assayed with triplicate. The $IC_{50}$ (ng/mL) was calculated according to Stewart and Watson method.

IgG Reformatting and Expression from scFv

The VL and VH gene of a scFv in a phagemid were cloned into IgG expression plasmid, pIgG (U.S. Pat. No. 5,736,137), to express secreted human IgG. The pIgG vector was linearized with NheI and KpnI restriction enzymes. VL and VH genes were PCR amplified separately, assembled into a 1.8 Kb fragment and infused into linearized pIgG vector. The pIgG expression vector was transfected into 293-F cells; the secreted IgG in the culture medium was purified with protein A agarose. The positive control IgGs: F10, FI6v3, C05, and CR8020 were expressed and purified with the same method described in this section.

$EC_{50}$ for Antibody-Antigen Interaction

The IgG $EC_{50}$ was determined by the titrations of IgG antibody on immobilized recombinant HA protein with ELISA. Four HA antigens, including H1N1 CA/09, H3N2 WN/05, H5N1 VN/04 or H7N9 AH/13 HA (0.5 μg per well) were coated in PBS buffer (pH 7.4) on 96-well immunoplates, and then blocked with 5% skim milk in PBST for 1 hour. In the meantime, two-fold serial dilutions of the antibody in PBST with 5% milk were performed and 11 different concentrations of the antibody were generated. After blocking, 100 μL diluted antibody samples were added to each well, and incubated for 1 hour under gentle shaking. The plate was washed 6 times with 300 μL PBST and then added with 100 μL 1:2000-diluted horse-radish peroxidase/anti-human IgG antibody conjugate in PBST with 5% milk for 1 hour incubation. The plates were washed 6 times with PBST buffer and twice with PBS, developed for 3 minutes with TMB substrate, quenched with 1.0 M HCl and read spectrophotometrically at 450 nm. $EC_{50}$ and sigmoidal curve fitting correlation coefficients were calculated. IgGs with the ELISA readings of 10 μg/mL IgG in the range of background ($OD_{450\ nm}$=0.04-0.05) were assigned as non-binding (NB).

Influenza Pseudo Virus-Based Microneutralization Assay

The H1N1 CA/09, H3N2 WN/05, or H7N9 AH/13 pseudo virus produced by co-transfection lentiviral core plasmid encoding luciferase (pHR'CMV-Luc), pCMV-R8.2 encoding HIV Gag-Pol, plasmids encoding TMPRSS2, respectively H1 A/California/04/2009 (Accession No. ACP41953.1), H3 A/Wisconsin/67/2005 (Accession No. AFH00648.1), H7 A/Anhui/1-BALF_RG17/2013 (Accession No. AHZ59831.1), and corresponding neuraminidase (pHR'CMV-Luc, pCMV-R8.2, plasmids expressing TMPRSS2, H1 A/California/04/2009, and N1 A/California/04/2009 were used). H5N1 pseudo virus was produced by co-transfection plasmid pLN4_3.Luc.R-E-, plasmids encoding H5 A/Vietnam/1203/2004 (Accession No. AY651334), and N1. After transfection overnight, cells were replenished with fresh medium and incubated for another 48 hours. Then, the supernatant were collected, filtered through 0.45 μm syringe filter, and stored at −80° C. until use. Microneutralization of pseudo virus was performed by incubated serial diluted antibodies with 100 $TCID_{50}$ pseudo virus for 45 minutes and then infect $1×10^4$ 293T cells in a well of 96 well plate. The medium was replenished with fresh medium 16-18 hours after infection. Sixty hours after infection, cells were lysed by lysis buffer and mixed with shaking for 15 minutes. Luciferase reagent was added to each well of white 96 well microplate. Cell lysate was transferred to corresponding well of white 96 well microplate prior to analysis of luciferase activity. The luciferase signal of virus-only control and that of negative control (no virus and no scFv) were set as 100% and 0% respectively. The neutralization percentage was calculated by the reduction of virus infection due to scFvs neutralization. Each concentration of diluted IgG was assayed with at least two repeats. The $IC_{50}$ (ng/mL) was calculated according to Stewart and Watson method.

Flow Cytometry Assay of Antibody Binding to HA-Expressing Stable Transfectants

H1 A/California/07/2009 (Accession No. ACP41953.1) and H5 A/Vietnam/1203/2004 (Accession No. AY651334) were cloned into pLAS2.PeGFP.Puro., which express green fluorescence protein (GFP) and puromycin resistant gene. HA-expressing stable transfectants were carried out by transfecting 293T cells separately with the full-length Influenza A pLAS2.H1 A/California/07/2009.PeGFP.Puro and pLAS2.H5 A/Vietnam/1203/2004.PeGFP.Puro. with polyethylenimine (PEI). Forty-eight hours post transfection, transfectants were selected with 2 μg/mL puromycin to obtained mixed stable transfectants. To analyze antibody binding to native HA protein, 293T H1 and H5 stable transfectants were stained with serial diluted IgGs at 4° C. for 30 minutes. Following the incubation, the cells were washed once with FACS buffer (1×PBS+0.05% FBS) and stained with the Alexa-Fluor 633-conjugated goat anti-human IgG secondary antibody. The cells were then incubated at 4° C. for another 30 minutes. After washing with FACS buffer twice, APC fluorescence signal of $GFP^+$ cells was analyzed by flow cytometry. Cells incubated with isotype negative control antibody were measured as negative control. Mean fluorescence intensity (MFI) of 10,000 $GFP^+$ cells was determined by software. Maximal MFI was the highest MFI in serial concentration of IgGs staining. $EC_{50}$ were determined by software. Mean fluorescence intensity (MFI) below 2.5 times of Do1 negative control IgG in independent experiment were defined as non-binding (NB).

Competition of Antibody-HA Interaction

To investigate the binding epitopes of selected anti-HA scFvs, a modified phage ELISA was used to detect the competition of the scFvs binding to recombinant HA with a panel of purified anti-HA IgGs. Test phages were fresh prepared. H1N1 CA/09 HA antigen (0.5 μg per well) were coated in PBS buffer (pH 7.4) on 96-well immunoplates overnight at 4° C., and blocked with 5% skim milk in PBST for 1 hour. After blocking, 1-3 μg purified anti-HA IgG were added to each well for 30 minutes under gently shaking and then added 50 μL test phage for another hour incubation. The plate was washed 6 times with 300 μL PBST and incubated 1 hour with horse-radish peroxidase/anti-M13 antibody conjugate (1:3000 dilution). The plates were washed six times with PBST buffer and twice with PBS, developed for 5 minutes with TMB substrate, quenched with 1.0 M HCl and read spectrophotometrically at 450 nm. Competition values were calculated by comparing each control sample without adding anti-HA IgGs.

S40 Fab Expression and Purification

S40 was expressed in mammalian cells (293-F cells) as a 6-His-tagged Fab with PEI transfection. The Fab expression vector was derived from the IgG expression plasmid, pIgG (U.S. Pat. No. 5,736,137), which did not contained CH2 and CH3 domains of heavy chain but with an additional 6-His-tag at C-terminus of CH1 domain of heavy chain, which forms disulfide bond with the constant domain of the light chain. Variable domain of light chain (VL) was subcloned into KpnI site while variable domain of heavy chain (VH) domain was subcloned into NheI site of the pIgG plasmid. S40 Fab was expressed by 293-F cells. 293-F cells were cultured to a final $1-1.5×10^6$ cells/mL in 293 expression medium, and incubated for 2-4 hours at 37° C. (8% $CO_2$, 110 rpm). S40 Fab construction was transfected into 293-F cells with PEI. Expressed S40 Fab was harvested from the supernatant 7-9 days or until cell viability drops below 60% after transfection. The S40 Fab was purified by $Ni^{2+}$-covalent bound column by gradient from 10 mM to 500 mM imidazole in TS solution (Tris-HCl 20 mM, NaCl 50 mM, pH 8.0). The fractions containing S40 Fab were concentrated and subjected to size exclusion chromatography with TS solution. The concentration of purified S40 Fab was measured by optical absorbance at 280 nm, and the purity and integrity was analyzed by reducing and non-reducing SDS-PAGE. The fractions containing S40 Fab were collected and stored in 4° C. or −80° C.

Crystallization and Data Collection

Crystals of HA1/S40-Fab complex were grown by mixing 1 μL protein solution with 1 μL reservoir solution using the sitting-drop vapor-diffusion method at 293° K. The crystals were obtained in a reservoir solution consisting of 8% (w/v) PEG 6000, 1N NaOH, 15% MPD, 0.1 M Na HEPES, pH 7.5. All crystals were flash-cooled and the diffraction patterns were recorded at cryogenic temperatures. The diffraction data of HA/S40-Fab complex crystals were collected at a wavelength of 0.90 Å on beamline BL44XU of the SPring-8 synchrotron in Japan using an MX-225 CCD detector. Diffraction data were processed and scaled to 3.35 Å resolution.

Structure Determination and Refinement

The HA1/S40-Fab complex crystals structure was determined by molecular replacement using MOLREP from the CCP4 suite with the IgG1 domain fragments (PDB entry 3W9D and 3HC4) and the HA1 fragment (PDB entry 3GBN) as the search models. The HA/S40-Fab complex crystals belong to space group C2, with two HA1/S40-Fab complexes in an asymmetric unit. Throughout the refinement, a randomly selected 5% of the data were set aside for cross-validation by the $R_{free}$ value. Manual modifications of the models were performed using the program Coot. The complex structure was refined using REFMAC5, from which $R_{work}$ and $R_{free}$ values of 23.0 and 27.5%, respectively, were obtained. Data-collection and final model statistics are shown in Table 1.

TABLE 1

Crystallography parameters for the S40-HA complex structure HA1/S40-Fab

| Data collection | |
| --- | --- |
| Wavelength (Å) | 0.9 |
| Space group | C2 |
| Cell dimensions (Å) | a = 200.40, |
|  | b = 133.64, |
|  | c = 133.14, |
|  | α = 90, |
|  | β = 110.47, |
|  | γ = 90 |
| Resolution (Å) | 25.0-3.35 (3.47-3.35) |
| Unique reflections | 47,477 |
| $R_{merge}$ (%) | 9.6 (64.5) |
| I/σ(I) | 17.3 (2.4) |
| Completeness | 99.6 (100.0) |
| Redundancy | 4.6 (4.7) |
| Refinement | |
| Resolution (Å) | 25.0-3.35 |
| No. of reflections $R_{work}/R_{free}$ | 34,487/1,826 |
| $R_{work}/R_{free}$ | 23.0/27.5 |
| No. of protein atoms/ Avg B factor (Å²) | 11,100/176.1 |
| RMSD | |
| Bond lengths (Å)/ Bond angles (°) | 0.01/1.49 |
| Ramachandran statistics (%)[b] | |
| Most favored | 75.0 |
| Additionally allowed | 22.8 |
| Generously allowed | 1.6 |
| Disallowed | 0.6 |

[a]Values corresponding to the highest resolution shells are shown in parentheses.
[b]Stereochemistry of the model was validated with PROCHECK.

Example 1

Anti-IAV Monoclonal scFvs Selected and Screened from the Phage-Displayed Synthetic Antibody Libraries on High Throughput Platform Success of high throughput discovery of anti-IAV neutralizing antibodies hinges on the sequences in the antibody libraries. Antibody discovery based on the M13 phage-displayed scFv libraries has been one of the most successful methodologies with high throughput capability. To fully exploit the advantages of the phage display methodology, 15 phage-displayed synthetic scFv libraries were developed, in which each of the scFv variants were stably folded with the CDR sequences encoding amino acid residues with high propensities for protein recognitions. The foldable scFv variants had been pre-selected during the library construction with protein A and protein L binding to ensure the fold ability of the scFv molecules expressed on the phage surface as fusion protein or in soluble form independent of the phage system. Such prerequisite embedded in the library construction procedure resulted in highly functional synthetic scFv libraries suitable for high throughput screening of the soluble scFv variants after the scFv variant population being reduced by several rounds of biopanning: most of the synthetic scFv variants existed in soluble scFv molecules with more than 1 μg/mL (or 33 nM) in crude E. coli culture in 96-well deep well plate overnight, feasible for many high throughput functional assays. By contrast to the unpredictable expression of the scFv molecules from conventional phage-displayed scFv libraries constructed from natural antibody gene repertoires, where the scFv molecules are frequently unable to be expressed in soluble form with sufficient concentration, the stable expression of functional synthetic scFvs enables a high throughput screening procedure effectively compatible with the high throughput micro-neutralization assay used in screening neutralizing antibodies against IAV infection.

Figure 1B:
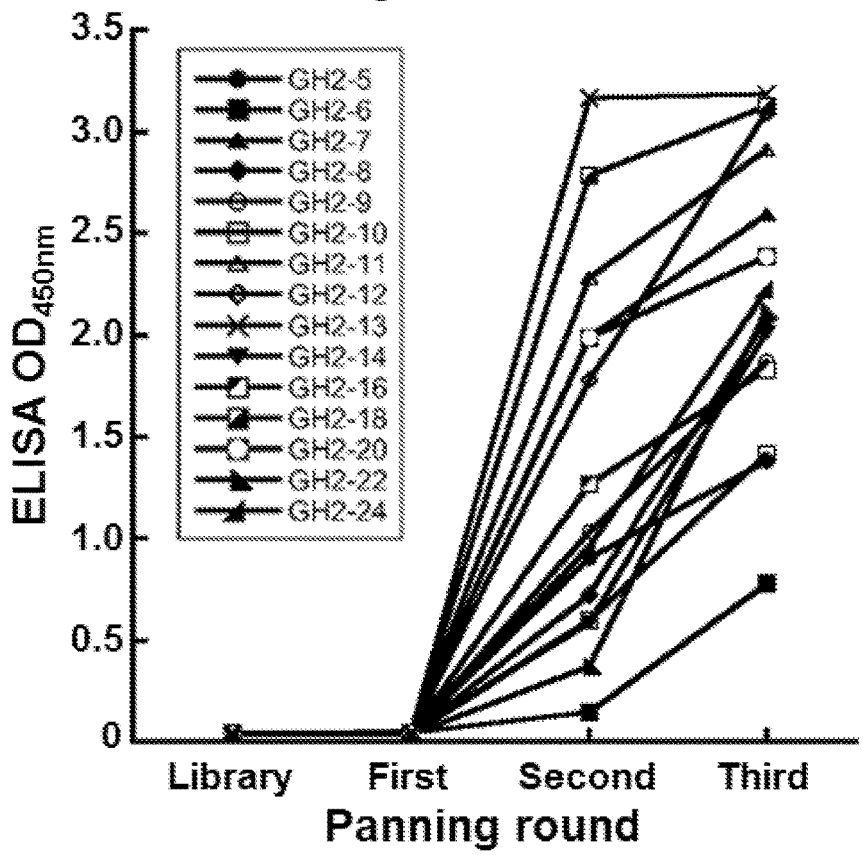
Figure 1C:
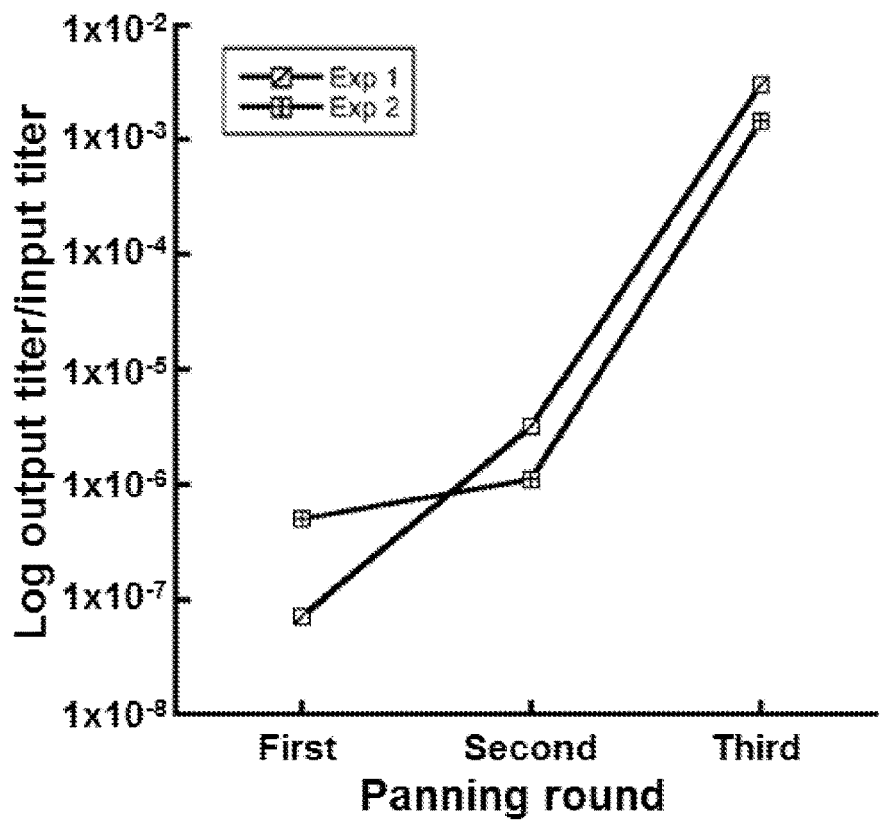
Figure 1D:
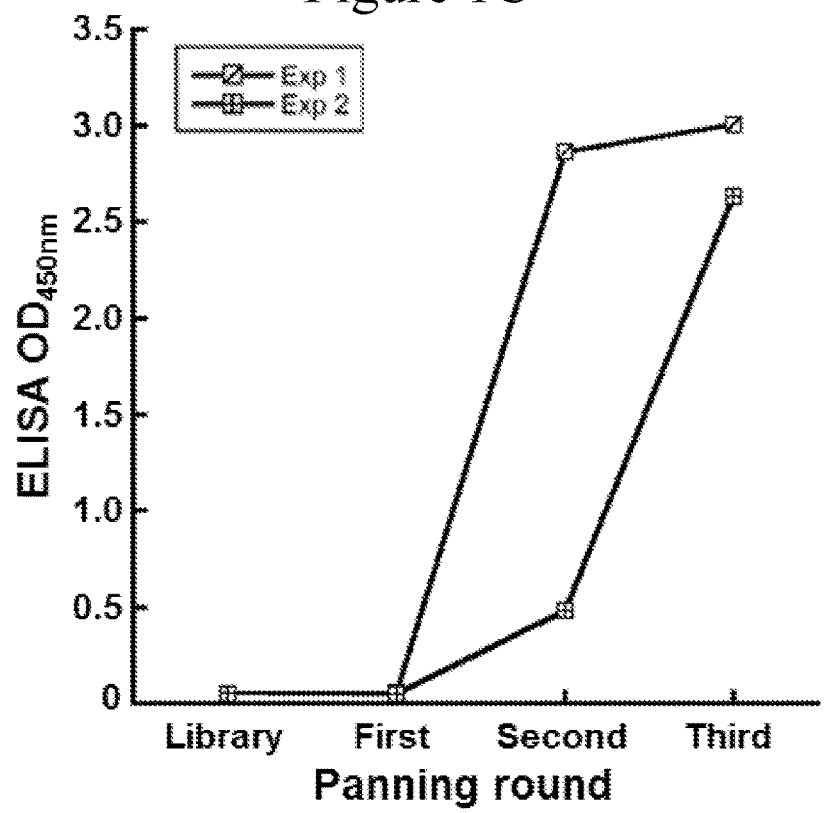

Anti-IAV antibodies were selected from the 15 phage-displayed scFv libraries through three rounds of biopanning with different pH in washing condition. The binding phase of the biopanning, where the phage-displayed scFvs bound to immobilized HA trimers of the 2009 pandemic IAV strain H1N1 CA/09, was always carried out at relatively neutral to weak basic pH (e.g., 7.4); the pH condition of the washing phase, where the unbound phage particles were removed from the antigen surface, was neutral for the first round, which was then followed by two rounds of biopanning with washing phase of pH5. The pH conditions mimic the pH change during the endocytosis of the host receptor-bound IAV from neutral environment to mildly acidic condition in the late endosome, where the conformational change of the HA trimer induced by the exposure to the acidic condition results in the infection of the host cell through the IAV membrane fusion with that of the host cell—surviving the acidic washing phase is a necessary condition for the scFv to neutralize IAV infection as a fusion inhibitor. For comparison, a control experiment with neutral binding and washing phase (pH 7.4) in all three rounds of biopanning was compared with one of the scFv libraries (GH2-13), so as to compare the effects of the acidic washing phase in the biopanning procedure. Both biopanning protocols were effective in resulting in HA binding scFvs after two to three rounds of biopanning (FIGS. 1A to 1D); the biopanning results indicate that all the 15 scFv libraries contain HA trimer-binding scFv variants, for which the soluble scFv molecules in the E. coli culture media are capable of binding to the surface-immobilized HA trimer.

Monoclonal scFvs were screened in high throughput format for folding into secreted soluble scFv, binding to immobilized HA trimer, and neutralizing IAV infection with micro-neutralization assay. The monoclonal scFvs were expressed in E. coli culture media in 96-well deep well plate, and the overnight culture supernatants without further scFv purification were ready for high throughput assays. One unique feature of the single-framework scFv variants from the synthetic GH2-5~24 scFv libraries is that the scFv molecule binds to protein A and protein L simultaneously in solution, and hence a sandwich ELISA with immobilized protein L and reporter-conjugated protein A can be used to identify well-folded scFv molecules. Only the well-folded scFvs (more than 90% of the selected clones) were assayed for HA-binding and IAV-neutralization. The ELISA data indicated that more than 5,000 monoclonal scFvs (including the antibodies P01 to P58 as listed in Table 2) and more than 100 monoclonal scFvs (including the antibodies S01 to S51 as listed in Table 2) were selected from all 15 scFv libraries by acidic washing phase (pH 5.0) and neutral washing phase (pH 7.4), respectively, in which each selected monoclonal scFv exhibited binding affinity to H1N1 CA/09 HA trimer (data not shown) The acidic condition in the washing phase improved the IAV-neutralization potencies of the selected scFvs by a small margin as compared to that of the control experiment (data not shown). Twenty eight sequence-wise non-redundant scFvs with IAV-neutralization potencies from both set of scFv variants were selected for IgG1 reformatting. The VL and VH sequences of these IgG1s are summarized in Table 2.

TABLE 2

VL and VH sequences of anti-influenza IgGs derived from synthetic antibody libraries

| Antibody | | VL sequence (SEQ ID NO) | VH sequence (SEQ ID NO) |
|---|---|---|---|
| The present 28 IgGs | P01 | 1 | 29 |
| | P03 | 2 | 30 |
| | P04 | 3 | 31 |
| | P05 | 4 | 32 |
| | P06 | 5 | 33 |
| | P10 | 6 | 34 |
| | P11 | 7 | 35 |
| | P12 | 8 | 36 |
| | P14 | 9 | 37 |
| | P25 | 10 | 38 |
| | P26 | 11 | 39 |
| | P28 | 12 | 40 |
| | P37 | 13 | 41 |
| | P38 | 14 | 42 |
| | P44 | 15 | 43 |
| | P47 | 16 | 44 |
| | P48 | 17 | 45 |
| | P58 | 18 | 46 |
| | S01 | 19 | 47 |
| | S06 | 20 | 48 |
| | S07 | 21 | 49 |
| | S10 | 22 | 50 |
| | S11 | 23 | 51 |
| | S29 | 24 | 52 |
| | S40 | 25 | 53 |
| | S45 | 26 | 54 |
| | S48 | 27 | 55 |
| | S51 | 28 | 56 |

TABLE 2-continued

VL and VH sequences of anti-influenza IgGs derived from synthetic antibody libraries

| Antibody | | VL sequence (SEQ ID NO) | VH sequence (SEQ ID NO) |
|---|---|---|---|
| Positive control | F10 | 63 | 64 |
| | FI6V3 | 65 | 66 |
| | C05 | 67 | 68 |
| | CR8020 | 69 | 70 |
| Negative control | Do1 | 71 | 72 |

\* Antibodies P01 to P58 were selected by acidic washing phase (pH5.0), and antibodies S01 to S51 were selected by neutral washing phase (pH7.4)

Antigen (HA trimer) binding affinity (50% maximal effective concentration—$EC_{50}$) and IAV-neutralization (50% maximal inhibitory concentration—$IC_{50}$) measurements for the 28 IgGs led to the confirmation of IAV-neutralizing IgGs with antigen-binding affinity approaching the affinity ceiling of affinity-matured anti-IAV antibodies derived from in-vivo immune systems (Table 3). Since the IgGs were selected and screened against the HA trimer of the strain H1N1 CA/09, the $EC_{50}$'s of these IgGs were approaching the affinity ceiling for the H1N1 CA/09 HA trimer of the control positive antibodies (F10 and FI6v3) reported previously (Table 3). Some of these IgGs were able to cross-react with the HA trimer of another group 1 subtype IAV H5N1 VN/04, albeit with lower affinities (Table 3). By contrast, none of the 28 IgGs cross-reacted with the HA trimers of group 2 subtype H3N2 WN/05 (Table 3), and only three IgGs were able to cross-react with the HA trimer of group 2 subtype H7N9 AH/13 (Table 3).

TABLE 3

Assessment of the neutralizing and binding potencies of anti-influenza IgGS derived from synthetic antibody libraries

| | | $EC_{50}$ of ELISA binding ($EC_{50}$ (ng/ml)) (correlation coefficient)) | | | | $EC_{50}$ of cell surface binding, ($EC_{50}$ (ng/ml)) (max. MFI)) | | | $IC_{50}$ of true virus neutralization (ng/ml) | $IC_{50}$ of pseudo virus neutralization (ng/ml) | | | |
|---|---|---|---|---|---|---|---|---|---|---|---|---|---|
| | | H1N1 | H3N2 | H5N1 | H7N9 | H1N1 | H3N2 | H5N1 | | H1N1 | H3N2 | H5N1 | H7N9 |
| Name | Grouping | CA/09 HA | WN/05 HA | ATN/04 HA | AH/13 HA | CA/09 HA | WN/05 HA | VN/04 HA | H1N1 CA/09 | H1N1 CA/09 | WN/05 | VN/04 | AH/13 |
| F10 | I | 12.15 (0.96) | NB | 20.98 (0.94) | NB | 1051 (9527) | NB (220) | 590 (10535) | 1256.98 | 11.9 | ND | 12 | >2 × 10⁵ |
| FI6V3 | I | 10.68 (0.96) | 78.93 (0.92) | 6.48 (0.92) | 313.63 (0.95) | 67 (10125) | 65 (16583) | 610 (13712) | 9214.55 | 21.3 | ND | 13 | 51 |
| C05 | | NB | 8.44 (0.95) | NB | NB | NB (86) | 130 (14588) | NB (547) | >5 × 10⁵ | >10⁵ | 10.17 | >2 × 10⁵ | >2 × 10⁵ |
| CR8020 | | NB | 19.37 (0.97) | NB | 68.99 (0.92) | NB (91) | 569 (18011) | NB (639) | >5 × 10⁵ | >10⁵ | 47.66 | >2 × 10⁵ | 52 |
| Do1 | | NB | NB | >10⁴ | NB | NB (228) | NB (278) | NB (313) | >5 × 10⁵ | >10⁵ | >2 × 10⁴ | >2 × 10⁵ | >2 × 10⁵ |
| P01 | II | 54.47 (0.94) | NB | 185.09 (0.96) | NB | 5900 (3668) | NB (342) | 5940 (1195) | >5 × 10⁵ | >10⁵ | >2 × 10⁴ | >2 × 10⁵ | >2 × 10⁵ |
| P03 | III | 15.61 (0.96) | >10⁴ | >10⁴ | NB | 494 (6022) | NB (147) | NB (216) | >5 × 10⁵ | >10⁵ | >2 × 10⁴ | >2 × 10⁵ | >2 × 10⁵ |
| P04 | I | 13.72 (0.97) | NB | >2000 | NB | 1920 (6244) | 3500 (2147) | 3260 (1603) | 62323 | 146.3 | >2 × 10⁴ | 185 | >2 × 10⁵ |
| P05 | I | 16.50 (0.97) | NB | NB | NB | 2060 (7950) | NB (176) | 190 (1723) | 289733 | 36.6 | >2 × 10⁴ | >2 × 10⁵ | >2 × 10⁵ |
| P06 | I | 5.59 (0.92) | NB | 238.05 (0.98) | NB | 1560 (11619) | NB (250) | 260 (1356) | 135818 | 135.9 | >2 × 10⁴ | 1256 | >2 × 10⁵ |
| P10 | I | 17.40 (0.97) | NB | NB | NB | 410 (9663) | NB (117) | NB (517) | >5 × 10⁵ | 464.9 | >2 × 10⁴ | >2 × 10⁵ | >2 × 10⁵ |
| P11 | I | 29.22 (0.95) | NB | >10⁴ | NB | 300 (8164) | NB (303) | 2420 (924) | 953155 | 104 | >2 × 10⁴ | 9293.78 | >2 × 10⁵ |

TABLE 3-continued

Assessment of the neutralizing and binding potencies of anti-influenza IgGS derived from synthetic antibody libraries

| | | EC$_{50}$ of ELISA binding (EC$_{50}$ (ng/ml)) (correlation coefficient)) | | | | EC$_{50}$ of cell surface binding, (EC$_{50}$ (ng/ml)) (max. MFI)) | | | IC$_{50}$ of true virus neutralization | IC$_{50}$ of pseudo virus neutralization | | | |
|---|---|---|---|---|---|---|---|---|---|---|---|---|---|
| | | H1N1 | H3N2 | H5N1 | H7N9 | H1N1 | H3N2 | H5N1 | (ng/ml) | (ng/ml) | | | |
| Name | Grouping | CA/09 HA | WN/05 HA | ATN/04 HA | AH/13 HA | CA/09 HA | WN/05 HA | VN/04 HA | H1N1 CA/09 | H1N1 CA/09 | H3N2 WN/05 | H5N1 VN/04 | H7N9 AH/13 |
| P12 | II | 54.94 (0.94) | >10$^4$ | NB | NB | 5860 (1995) | NB (209) | 6540 (883) | >5 × 10$^5$ | >10$^5$ | >2 × 10$^4$ | >2 × 10$^5$ | >2 × 10$^5$ |
| P14 | III | 11.71 (0.96) | NB | NB | NB | 125 (8337) | NB (154) | NB (328) | 4393351 | >10$^5$ | >2 × 10$^4$ | >2 × 10$^5$ | >2 × 10$^5$ |
| P25 | III | 138.93 (0.95) | NB | NB | NB | 761 (2376) | NB (152) | NB (318) | >5 × 10$^5$ | >10$^5$ | >2 × 10$^4$ | >2 × 10$^5$ | >2 × 10$^5$ |
| P26 | I | 11.91 (0.96) | NB | 26.55 (0.92) | 75.05 (0.94) | 2035 (8923) | NB (120) | 650 (6402) | 29596 | 549.3 | >2 × 10$^4$ | 85 | >2 × 10$^5$ |
| P28 | II | 797.79 (0.91) | NB | NB | NB | NB (168) | NB (127) | NB (193) | >5 × 10$^5$ | >10$^5$ | >2 × 10$^4$ | >2 × 10$^5$ | >2 × 10$^5$ |
| P37 | I | 235.68 (0.98) | NB | NB | NB | 420 (5028) | NB (199) | 1180 (644) | >5 × 10$^5$ | 1674 | >2 × 10$^4$ | >2 × 10$^5$ | >2 × 10$^5$ |
| P38 | III | 94.39 (0.96) | NB | NB | NB | 3160 (988) | NB (137) | NB (240) | >5 × 10$^5$ | >10$^5$ | >2 × 10$^4$ | >2 × 10$^5$ | >2 × 10$^5$ |
| P44 | II | 15.03 (0.97) | NB | 100 (0.96) | 162.86 (0.94) | 466 (8478) | NB (127) | NB (188) | >5 × 10$^5$ | >10$^5$ | >2 × 10$^4$ | >2 × 10$^5$ | >2 × 10$^5$ |
| P47 | III | 9.62 (0.96) | NB | NB | NB | 610 (10241) | NB (175) | NB (396) | >5 × 10$^5$ | >10$^5$ | >2 × 10$^4$ | >2 × 10$^5$ | >2 × 10$^5$ |
| P48 | III | 15.36 (0.97) | NB | NB | NB | 2400 (7865) | NB (258) | NB (474) | >5 × 10$^5$ | >10$^5$ | >2 × 10$^4$ | >2 × 10$^5$ | >2 × 10$^5$ |
| P58 | II | 22.74 (0.96) | NB | >10$^4$ | 503.58 (0.93) | 250 (6288) | 3581 (697) | 366 (6713) | >5 × 10$^5$ | >10$^5$ | >2 × 10$^4$ | >2 × 10$^5$ | >2 × 10$^5$ |
| S01 | III | 12.18 (0.96) | NB | NB | NB | 384 (8428) | NB (178) | NB (306) | >5 × 10$^5$ | >10$^5$ | >2 × 10$^4$ | >2 × 10$^5$ | >2 × 10$^5$ |
| S06 | II | 46.70 (0.97) | NB | 310.98 (0.97) | NB | 3982 (1648) | NB (135) | NB (249) | >5 × 10$^5$ | >10$^5$ | >2 × 10$^4$ | >2 × 10$^5$ | >2 × 10$^5$ |
| S07 | III | 11.42 (0.96) | NB | NB | NB | 1610 (10791) | 3710 (410) | 4980 (863) | >5 × 10$^5$ | >10$^5$ | >2 × 10$^4$ | >2 × 10$^5$ | >2 × 10$^5$ |
| S10 | I | 14.00 (0.97) | NB | 259.21 (0.97) | NB | 3380 (10696) | 7860 (511) | 790 (1099) | 1562813 | 349.1 | >2 × 10$^4$ | 267 | >2 × 10$^5$ |
| S11 | II | 26.79 (0.98) | NB | 78.14 (0.90) | NB | 4070 (5600) | NB (207) | NB (434) | >5 × 10$^5$ | >10$^5$ | >2 × 10$^4$ | >2 × 10$^5$ | >2 × 10$^5$ |
| S29 | I | 22.27 (0.98) | NB | >10$^4$ | NB | 4220 (6276) | NB (188) | NB (367) | >5 × 10$^5$ | 672.2 | >2 × 10$^4$ | >2 × 10$^5$ | >2 × 10$^5$ |
| S40 | III | 16.32 (0.96) | NB | NB | NB | 460 (8626) | NB (109) | 2850 (724) | 435924 | >10$^5$ | >2 × 10$^4$ | >2 × 10$^5$ | >2 × 10$^5$ |
| S45 | II | 20.61 (0.96) | NB | 230.35 (0.97) | NB | 4470 (2473) | 15800 (529) | NB (451) | >5 × 10$^5$ | >10$^5$ | >2 × 10$^4$ | >2 × 10$^5$ | >2 × 10$^5$ |
| S48 | II | 12.50 (0.97) | NB | 73.75 (0.91) | NB | 4860 (6243) | NB (122) | 1920 (875) | >5 × 10$^5$ | >10$^5$ | >2 × 10$^4$ | >2 × 10$^5$ | >2 × 10$^5$ |
| S51 | III | 23.38 (0.96) | NB | NB | NB | 754 (6290) | NB (340) | NB (452) | >5 × 10$^5$ | >10$^5$ | >2 × 10$^4$ | >2 × 10$^5$ | >2 × 10$^5$ |

To address the biological relevance of the ELISA-based EC$_{50}$'s, the MFI-based EC$_{50}$ was determined by flow cytometry measuring the IgG-HA trimer binding on 293T cells over-expressing the HA trimers on the cell surfaces (Table 3). Qualitatively, all the IgGs binding to ELISA surface-immobilized H1N1 CA/09 HA trimer also bound to 293T surface expressed H1N1 CA/09 HA trimer (Table 3), indicating that immobilization of HA trimers on solid ELISA surface did not substantially change the biologically relevant structure of the HA trimer. As expected, the IgGs were also cross-reacted with the cell surface-expressed H5N1 VN/05 HA trimer, but with significant reduction of the antibody-HA affinities (Table 3). Also as expected, none of the IgGs cross-reacted with the cell surface-expressed H3N2 WN/05 HA trimer. The H7N9 AH/13 HA trimer was unable to be expressed on 293T cell surface and hence the few IgGs cross-reacting with the H7N9 AH/13 HA trimer based on the ELISA measurements in Table 3 could not be confirmed in the cell-based binding experiments. Nevertheless, pseudo virus-based micro-neutralization assays indicated that these potentially cross-reacting IgGs could not neutralize the H7N9 AH/13 IAV infection (Table 3).

Pseudo virus-based micro-neutralization assays indicated that about a quarter of the IgGs binding the H1N1 CA/09 HA trimer could neutralize the pseudo virus infection to the extent, for which the IC$_{50}$'s were measurable in the micro-neutralization assay (Table 3), and some of the IgGs cross-reacting with the H5N1 VN/04 HA trimer were also neutralizing antibodies against the H5N1 VN/04 pseudo virus (Table 3). As expected from the binding assays, these IgGs did not have neutralizing effect against the group 2 pseudo viruses (Table 3).

To address the biological relevance of the pseudo virus-based micro neutralization assays, the IC$_{50}$ of the IgGs with IAV strain H1N1 CA/09 was determined, and the IC$_{50}$ measured by the two micro-neutralization assays were compared. Only a subset of the neutralizing IgGs identified by the pseudo virus-based micro-neutralization assays was able to neutralize the real virus infection to the extent, for which the IC$_{50}$ were measurable in the micro-neutralization assay (Table 3), indicating that the pseudo virus-based micro-neutralization assay was more sensitive in comparison with the micro-neutralization assay with the real virus. Overall, only the IgGs produced by the acidic washing phase are neutralizing antibodies, indicating that the acidic condition in the washing phase of the phage display selection procedure does enhance the chance of discovering neutralizing antibodies.

Example 2

The Anti-IAV Neutralizing Antibodies Derived From the Synthetic Antibody Libraries Exhibited Binding Affinity to the Stem Epitopes on the HA Trimer The neutralization mechanism of the recombinant IgGs was epitope-dependent. Competition measurements of the 28 recombinant anti-HA IgGs in Table 3 indicated that the epitopes of these IgGs on the H1N1 CA/09 HA trimer could be classified into three major groups (Tables 3). The epitope group classification for the IgGs derived from the acidic washing phase was strikingly similar to the IgGs derived from the neutral washing phase (Table 3), indicating that the biopanning protocol and the CDR-H3 sequence length and amino acid composition did not dictate the epitope group distribution of the anti-HA antibodies from the synthetic antibody libraries. Out of the scope of the 28 recombinant anti-HA IgGs in present invention, IgG with the group I epitope was a necessary and sufficient condition for the IgG to be an anti-IAV neutralizing antibody; none of the IgGs with epitopes in group II and III were neutralizing antibodies based on the pseudo virus-based micro-neutralization assays (Table 3). Since both epitopes of the positive control broadly neutralizing antibodies F10 and FI6v3 belonged to epitope group I and have been known to bind to the stem region of the HA trimer with sub-nanomolar affinity to HA trimers, the group I IgGs were anticipated binding to the stem region of the HA trimer with high affinity as well; the stem epitopes have been identified as one of the vulnerable regions on HA trimers targeted by many anti-IAV broadly neutralizing antibodies.

Antibodies in epitope group III bound to epitopes that were not accessible in pre-fusion HA trimer structure. IgG S40 in group III exhibited weak neutralization potency against IAV H1N1 CA/09 based on the real virus micro-neutralization assay (Table 3) and thus was selected for epitope mapping with Fab-HA complex structure crystallography. The Fab(S40)-HA(H1N1 CA/09) complex structure has been solved to 3.28 Å resolution (Table 1), revealing the binding of the S40 Fab to the inner surface of the HA1 head domain that formed part of the trimer interface and was not accessible as an antibody epitope in the pre-fusion HA trimer structure (data not shown). S40 IgG exhibited high affinity to H1N1 CA/09 HA trimer, as indicated by the $EC_{50}$'s based on ELISA and MFI measurements (Table 3), suggesting that S40 IgG's epitope on the HA trimer was indeed accessible in both immobilized or cell surface-expressed form of the HA trimer. Moreover, the weak neutralizing potency of the S40 IgG against IAV H1N1 CA/09 (Table 3) suggested that the epitope on the HA trimer could be exposed (at least transiently) for S40 antibody binding, leading to the neutralization of the infection by IAV H1N1 CA/09.

In summary, passive immunotherapy with anti-LAV neutralizing recombinant antibodies is one of the viable strategies mitigating threats of epidemic and pandemic IAV infection. Technological platform for high throughput discovery of anti-IAV neutralizing recombinant antibodies is particularly desirable during the outbreak of pandemics when candidate recombinant antibodies need to be rapidly developed before large population infection causing significant mortality, morbidity and economic loss, in particular when affinity matured human antibodies with neutralizing efficacy against the pandemic strain are not available. High throughput screening of functional neutralizing antibodies requires production of thousands monoclonal antibodies in high throughput format with enough concentration for functional assays; the phage-displayed synthetic scFv libraries with scFv expression quality control meet the prerequisite of the high throughput screening for anti-IAV neutralizing recombinant antibodies, as demonstrated in this work. Once the recombinant HA trimer and the pseudo virus of the pandemic IAV strain become available, neutralizing IgG candidates suitable for passive immunotherapy should be attained within one month by following through the high throughput procedure. With continuing advancement in designing and constructing synthetic scFv libraries containing diverse functional antibody fragments, this technological platform not only provides a promising option in mitigating the threats of IAV pandemics; the technology can also provide options to develop recombinant antibody candidates for passive immunotherapy treating other newly emerging viral infections.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A neutralizing antibody comprising
a VL domain comprising SEQ ID NO: 5; and
a VH domain comprising SEQ ID NO: 33.

2. The neutralizing antibody of claim 1, wherein the antibody is produced by a method comprising,
   (a) providing a phage-displayed single-chain variable fragment (scFv) library that comprises a plurality of phage-displayed scFvs, wherein the heavy chain variable (VH) domain of each phage-displayed scFvs has a binding affinity to protein A, and the light chain variable (VL) domain of each phage-displayed scFvs has a binding affinity to protein L;
   (b) exposing the phage-displayed scFv library of the step (a) to a viral antigen derived from the virus;
   (c) selecting, from the phage-displayed scFv library of the step (b), a plurality of phages that express scFvs exhibiting binding affinity to the viral antigen under an acidic condition;
   (d) respectively enabling the plurality of phages selected in the step (c) to express a plurality of soluble scFvs;
   (e) exposing the plurality of soluble scFvs of the step (d) to the virus;
   (f) determining the respective neutralizing efficacy of the plurality of soluble scFvs in the step (e); and
   (g) based on the results determined in the step (f), selecting one soluble scFv that exhibits superior efficacy over the other soluble scFvs of the plurality of soluble scFvs as the neutralizing antibody.

* * * * *

SEQUENCE LISTING

```
<160> NUMBER OF SEQ ID NOS: 72

<210> SEQ ID NO 1
<211> LENGTH: 108
<212> TYPE: PRT
<213> ORGANISM: Artificial Sequence
<220> FEATURE:
<223> OTHER INFORMATION: synthesized-P01_VL

<400> SEQUENCE: 1
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Trp Tyr
            20                  25                  30

Val Ala Trp Tyr Gln Gln Lys Pro Gly Lys Ala Pro Lys Leu Leu Ile
        35                  40                  45

Tyr Gly Ser Thr Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Ser Pro Leu
                85                  90                  95

Thr Phe Gly Gln Gly Thr Lys Val Glu Ile Lys Arg
            100                 105

<210> SEQ ID NO 2
<211> LENGTH: 108
<212> TYPE: PRT
<213> ORGANISM: Artificial Sequence
<220> FEATURE:
<223> OTHER INFORMATION: synthesized-P03_VL

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Tyr
            20                  25                  30

Val Ala Trp Tyr Gln Gln Lys Pro Gly Lys Ala Pro Lys Leu Leu Ile
        35                  40                  45

Ser Trp Ser Gly Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Val
                85                  90                  95

Thr Phe Gly Gln Gly Thr Lys Val Glu Ile Lys Arg
            100                 105

<210> SEQ ID NO 3
<211> LENGTH: 108
<212> TYPE: PRT
<213> ORGANISM: Artificial Sequence
<220> FEATURE:
<223> OTHER INFORMATION: synthesized-P04_VL

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Gly Ser
            20                  25                  30

Val Ala Trp Tyr Gln Gln Lys Pro Gly Lys Ala Pro Lys Leu Leu Ile
        35                  40                  45

Ser Ser Ser Ala Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Tyr Pro Leu
                85                  90                  95
```

Thr Phe Gly Gln Gly Thr Lys Val Glu Ile Lys Arg
            100                 105

<210> SEQ ID NO 4
<211> LENGTH: 108
<212> TYPE: PRT
<213> ORGANISM: Artificial Sequence
<220> FEATURE:
<223> OTHER INFORMATION: synthesized-P05_VL

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Ser
            20                  25                  30

Val Ala Trp Tyr Gln Gln Lys Pro Gly Lys Ala Pro Lys Leu Leu Ile
        35                  40                  45

Ser Ser Ser Pro Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gln Gly Thr Lys Val Glu Ile Lys Arg
            100                 105

<210> SEQ ID NO 5
<211> LENGTH: 108
<212> TYPE: PRT
<213> ORGANISM: Artificial Sequence
<220> FEATURE:
<223> OTHER INFORMATION: synthesized-P06_VL

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Gly Gly
            20                  25                  30

Val Ala Trp Tyr Gln Gln Lys Pro Gly Lys Ala Pro Lys Leu Leu Ile
        35                  40                  45

Ser Gly Thr Ser Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Asn Phe Pro Ile
                85                  90                  95

Thr Phe Gly Gln Gly Thr Lys Val Glu Ile Lys Arg
            100                 105

<210> SEQ ID NO 6
<211> LENGTH: 108
<212> TYPE: PRT
<213> ORGANISM: Artificial Sequence
<220> FEATURE:
<223> OTHER INFORMATION: synthesized-P10_VL

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ser Asn
            20                  25                  30

Val Ala Trp Tyr Gln Gln Lys Pro Gly Lys Ala Pro Lys Leu Leu Ile
        35                  40                  45

Tyr Trp Ala Gly Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Asp Phe Pro Ile
                85                  90                  95

Thr Phe Gly Gln Gly Thr Lys Val Glu Ile Lys Arg
            100                 105

<210> SEQ ID NO 7
<211> LENGTH: 108
<212> TYPE: PRT
<213> ORGANISM: Artificial Sequence
<220> FEATURE:
<223> OTHER INFORMATION: synthesized-P11_VL

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Asn Asn
            20                  25                  30

Val Ala Trp Tyr Gln Gln Lys Pro Gly Lys Ala Pro Lys Leu Leu Ile
        35                  40                  45

Ser Tyr Ala Ser Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Gly Gly Pro Val
                85                  90                  95

Thr Phe Gly Gln Gly Thr Lys Val Glu Ile Lys Arg
            100                 105

<210> SEQ ID NO 8
<211> LENGTH: 108
<212> TYPE: PRT
<213> ORGANISM: Artificial Sequence
<220> FEATURE:
<223> OTHER INFORMATION: synthesized-P12_VL

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Tyr Trp
            20                  25                  30

Val Ala Trp Tyr Gln Gln Lys Pro Gly Lys Ala Pro Lys Leu Leu Ile
        35                  40                  45

Tyr Trp Thr Ser Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asn Trp Pro Ile
                85                  90                  95

Thr Phe Gly Gln Gly Thr Lys Val Glu Ile Lys Arg
            100                 105

<210> SEQ ID NO 9
<211> LENGTH: 108
<212> TYPE: PRT
<213> ORGANISM: Artificial Sequence
<220> FEATURE:
<223> OTHER INFORMATION: synthesized-P14_VL

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Phe Tyr
            20                  25                  30

Val Ala Trp Tyr Gln Gln Lys Pro Gly Lys Ala Pro Lys Leu Leu Ile
        35                  40                  45

Ser Trp Ser Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Leu
                85                  90                  95

Thr Phe Gly Gln Gly Thr Lys Val Glu Ile Lys Arg
            100                 105

<210> SEQ ID NO 10
<211> LENGTH: 108
<212> TYPE: PRT
<213> ORGANISM: Artificial Sequence
<220> FEATURE:
<223> OTHER INFORMATION: synthesized-P25_VL

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Tyr
            20                  25                  30

Val Ala Trp Tyr Gln Gln Lys Pro Gly Lys Ala Pro Lys Leu Leu Ile
        35                  40                  45

Ser Gly Ser Arg Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Ile
                85                  90                  95

Thr Phe Gly Gln Gly Thr Lys Val Glu Ile Lys Arg
            100                 105

<210> SEQ ID NO 11
<211> LENGTH: 108
<212> TYPE: PRT
<213> ORGANISM: Artificial Sequence
<220> FEATURE:
<223> OTHER INFORMATION: synthesized-P26_VL

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Ser Gly
            20                  25                  30

```
Val Ala Trp Tyr Gln Gln Lys Pro Gly Lys Ala Pro Lys Leu Leu Ile
            35                  40                  45

Tyr Gly Thr Thr Tyr Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Phe Leu Leu
                 85                  90                  95

Thr Phe Gly Gln Gly Thr Lys Val Glu Ile Lys Arg
                100                 105
```

<210> SEQ ID NO 12
<211> LENGTH: 108
<212> TYPE: PRT
<213> ORGANISM: Artificial Sequence
<220> FEATURE:
<223> OTHER INFORMATION: synthesized-P28_VL

<400> SEQUENCE: 12

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Trp Tyr Ser
                20                  25                  30

Val Ala Trp Tyr Gln Gln Lys Pro Gly Lys Ala Pro Lys Leu Leu Ile
            35                  40                  45

Tyr Phe Ala Thr Gly Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Phe Asn Trp Pro Val
                 85                  90                  95

Thr Phe Gly Gln Gly Thr Lys Val Glu Ile Lys Arg
                100                 105
```

<210> SEQ ID NO 13
<211> LENGTH: 108
<212> TYPE: PRT
<213> ORGANISM: Artificial Sequence
<220> FEATURE:
<223> OTHER INFORMATION: synthesized-P37_VL

<400> SEQUENCE: 13

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Gly Asn Asp
                20                  25                  30

Val Ala Trp Tyr Gln Gln Lys Pro Gly Lys Ala Pro Lys Leu Leu Ile
            35                  40                  45

Ser Ser Ala Arg Gly Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Phe Pro Ile
                 85                  90                  95

Thr Phe Gly Gln Gly Thr Lys Val Glu Ile Lys Arg
                100                 105
```

<210> SEQ ID NO 14

```
<211> LENGTH: 108
<212> TYPE: PRT
<213> ORGANISM: Artificial Sequence
<220> FEATURE:
<223> OTHER INFORMATION: synthesized-P38_VL

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Tyr
            20                  25                  30

Val Ala Trp Tyr Gln Gln Lys Pro Gly Lys Ala Pro Lys Leu Leu Ile
        35                  40                  45

Ser Trp Pro Gly Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Leu
                85                  90                  95

Thr Phe Gly Gln Gly Thr Lys Val Glu Ile Lys Arg
            100                 105

<210> SEQ ID NO 15
<211> LENGTH: 108
<212> TYPE: PRT
<213> ORGANISM: Artificial Sequence
<220> FEATURE:
<223> OTHER INFORMATION: synthesized-P44_VL

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Asn
            20                  25                  30

Val Ala Trp Tyr Gln Gln Lys Pro Gly Lys Ala Pro Lys Leu Leu Ile
        35                  40                  45

Tyr Trp Ser Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Phe Pro Val
                85                  90                  95

Thr Phe Gly Gln Gly Thr Lys Val Glu Ile Lys Arg
            100                 105

<210> SEQ ID NO 16
<211> LENGTH: 108
<212> TYPE: PRT
<213> ORGANISM: Artificial Sequence
<220> FEATURE:
<223> OTHER INFORMATION: synthesized-P47_VL

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Tyr Tyr
            20                  25                  30

Val Ala Trp Tyr Gln Gln Lys Pro Gly Lys Ala Pro Lys Leu Leu Ile
        35                  40                  45
```

```
Ser Gly Ser Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Trp Pro Leu
                85                  90                  95

Thr Phe Gly Gln Gly Thr Lys Val Glu Ile Lys Arg
            100                 105

<210> SEQ ID NO 17
<211> LENGTH: 108
<212> TYPE: PRT
<213> ORGANISM: Artificial Sequence
<220> FEATURE:
<223> OTHER INFORMATION: synthesized-P48_VL

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Ser Tyr
                20                  25                  30

Val Ala Trp Tyr Gln Gln Lys Pro Gly Lys Ala Pro Lys Leu Leu Ile
            35                  40                  45

Ser Tyr Thr Ser Tyr Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Ile
                85                  90                  95

Thr Phe Gly Gln Gly Thr Lys Val Glu Ile Lys Arg
            100                 105

<210> SEQ ID NO 18
<211> LENGTH: 108
<212> TYPE: PRT
<213> ORGANISM: Artificial Sequence
<220> FEATURE:
<223> OTHER INFORMATION: synthesized-P58_VL

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Ser Tyr
                20                  25                  30

Val Ala Trp Tyr Gln Gln Lys Pro Gly Lys Ala Pro Lys Leu Leu Ile
            35                  40                  45

Ser Ser Ser Arg Gly Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Ile
                85                  90                  95

Thr Phe Gly Gln Gly Thr Lys Val Glu Ile Lys Arg
            100                 105

<210> SEQ ID NO 19
<211> LENGTH: 108
<212> TYPE: PRT
<213> ORGANISM: Artificial Sequence
```

<220> FEATURE:
<223> OTHER INFORMATION: synthesized-S01_VL

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Tyr
            20                  25                  30

Val Ala Trp Tyr Gln Gln Lys Pro Gly Lys Ala Pro Lys Leu Leu Ile
        35                  40                  45

Ser Phe Pro Ser Ser Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Gly Pro Val
                85                  90                  95

Thr Phe Gly Gln Gly Thr Lys Val Glu Ile Lys Arg
            100                 105

<210> SEQ ID NO 20
<211> LENGTH: 108
<212> TYPE: PRT
<213> ORGANISM: Artificial Sequence
<220> FEATURE:
<223> OTHER INFORMATION: synthesized-S06_VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Trp
            20                  25                  30

Val Ala Trp Tyr Gln Gln Lys Pro Gly Lys Ala Pro Lys Leu Leu Ile
        35                  40                  45

Tyr Gly Thr Thr Phe Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Gly Pro Leu
                85                  90                  95

Thr Phe Gly Gln Gly Thr Lys Val Glu Ile Lys Arg
            100                 105

<210> SEQ ID NO 21
<211> LENGTH: 108
<212> TYPE: PRT
<213> ORGANISM: Artificial Sequence
<220> FEATURE:
<223> OTHER INFORMATION: synthesized-S07_VL

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Tyr
            20                  25                  30

Val Ala Trp Tyr Gln Gln Lys Pro Gly Lys Ala Pro Lys Leu Leu Ile
        35                  40                  45

Ser Tyr Ala Ser Phe Leu Tyr Ser Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Phe Asn Trp Pro Val
                 85                  90                  95

Thr Phe Gly Gln Gly Thr Lys Val Glu Ile Lys Arg
            100                 105
```

<210> SEQ ID NO 22
<211> LENGTH: 108
<212> TYPE: PRT
<213> ORGANISM: Artificial Sequence
<220> FEATURE:
<223> OTHER INFORMATION: synthesized-S10_VL

<400> SEQUENCE: 22

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Tyr Tyr
                20                  25                  30

Val Ala Trp Tyr Gln Gln Lys Pro Gly Lys Ala Pro Lys Leu Leu Ile
             35                  40                  45

Phe Trp Ser Thr Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asp Ser Pro Met
                 85                  90                  95

Thr Phe Gly Gln Gly Thr Lys Val Glu Ile Lys Arg
            100                 105
```

<210> SEQ ID NO 23
<211> LENGTH: 108
<212> TYPE: PRT
<213> ORGANISM: Artificial Sequence
<220> FEATURE:
<223> OTHER INFORMATION: synthesized-S11_VL

<400> SEQUENCE: 23

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Tyr Ser Trp
                20                  25                  30

Val Ala Trp Tyr Gln Gln Lys Pro Gly Lys Ala Pro Lys Leu Leu Ile
             35                  40                  45

Tyr Tyr Ser Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asn Gly Pro Leu
                 85                  90                  95

Thr Phe Gly Gln Gly Thr Lys Val Glu Ile Lys Arg
            100                 105
```

<210> SEQ ID NO 24
<211> LENGTH: 108
<212> TYPE: PRT
<213> ORGANISM: Artificial Sequence
<220> FEATURE:
<223> OTHER INFORMATION: synthesized-S29_VL

```
<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Gly Gly
            20                  25                  30

Val Ala Trp Tyr Gln Gln Lys Pro Gly Lys Ala Pro Lys Leu Leu Ile
        35                  40                  45

Tyr Trp Ser Ser Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Gly Pro Ile
                85                  90                  95

Thr Phe Gly Gln Gly Thr Lys Val Glu Ile Lys Arg
            100                 105

<210> SEQ ID NO 25
<211> LENGTH: 108
<212> TYPE: PRT
<213> ORGANISM: Artificial Sequence
<220> FEATURE:
<223> OTHER INFORMATION: synthesized-S40_VL

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Phe Tyr
            20                  25                  30

Val Ala Trp Tyr Gln Gln Lys Pro Gly Lys Ala Pro Lys Leu Leu Ile
        35                  40                  45

Ser Trp Ser Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Leu
                85                  90                  95

Thr Phe Gly Gln Gly Thr Lys Val Glu Ile Lys Arg
            100                 105

<210> SEQ ID NO 26
<211> LENGTH: 108
<212> TYPE: PRT
<213> ORGANISM: Artificial Sequence
<220> FEATURE:
<223> OTHER INFORMATION: synthesized-S45_VL

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Trp Trp
            20                  25                  30

Val Ala Trp Tyr Gln Gln Lys Pro Gly Lys Ala Pro Lys Leu Leu Ile
        35                  40                  45

Tyr Gly Ala Arg Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Phe Asn Gly Pro Leu
            85                  90                  95

Thr Phe Gly Gln Gly Thr Lys Val Glu Ile Lys Arg
            100                 105

<210> SEQ ID NO 27
<211> LENGTH: 108
<212> TYPE: PRT
<213> ORGANISM: Artificial Sequence
<220> FEATURE:
<223> OTHER INFORMATION: synthesized-S48_VL

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Trp Trp
            20                  25                  30

Val Ala Trp Tyr Gln Gln Lys Pro Gly Lys Ala Pro Lys Leu Leu Ile
            35                  40                  45

Tyr Gly Thr Arg Trp Leu Tyr Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Gln Tyr Tyr Ser Gly Pro Ile
            85                  90                  95

Thr Phe Gly Gln Gly Thr Lys Val Glu Ile Lys Arg
            100                 105

<210> SEQ ID NO 28
<211> LENGTH: 108
<212> TYPE: PRT
<213> ORGANISM: Artificial Sequence
<220> FEATURE:
<223> OTHER INFORMATION: synthesized-S51_VL

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Tyr
            20                  25                  30

Val Ala Trp Tyr Gln Gln Lys Pro Gly Lys Ala Pro Lys Leu Leu Ile
            35                  40                  45

Ser Tyr Thr Thr Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Ser Pro Val
            85                  90                  95

Thr Phe Gly Gln Gly Thr Lys Val Glu Ile Lys Arg
            100                 105

<210> SEQ ID NO 29
<211> LENGTH: 118
<212> TYPE: PRT
<213> ORGANISM: Artificial Sequence
<220> FEATURE:
<223> OTHER INFORMATION: synthesized-P01_VH

<400> SEQUENCE: 29

Glu Val Gln Leu Val Glu Ser Gly Gly Gly Leu Val Gln Pro Gly Gly

```
           1               5                  10                 15
         Ser Leu Arg Leu Ser Cys Ala Ala Ser Gly Phe Thr Ile Gly Asp Gly
                         20                  25                 30

Ser Ile His Trp Val Arg Gln Ala Pro Gly Lys Gly Leu Glu Trp Val
                         35                  40                 45

Ala Trp Ile Gly Pro Tyr Gly Gly Ser Thr Phe Tyr Ala Asp Ser Val
                 50                  55                 60

Lys Gly Arg Phe Thr Ile Ser Ala Asp Thr Ser Lys Asn Thr Ala Tyr
         65                      70                  75                 80

Leu Gln Met Asn Ser Leu Arg Ala Glu Asp Thr Ala Val Tyr Tyr Cys
                         85                  90                 95

Ala Arg Phe Phe Trp Gly Ile Asn Met Asp Tyr Trp Gly Gln Gly Thr
                         100                 105                110

Leu Val Thr Val Ser Ser
                 115

<210> SEQ ID NO 30
<211> LENGTH: 123
<212> TYPE: PRT
<213> ORGANISM: Artificial Sequence
<220> FEATURE:
<223> OTHER INFORMATION: synthesized-P03_VH

<400> SEQUENCE: 30

Glu Val Gln Leu Val Glu Ser Gly Gly Gly Leu Val Gln Pro Gly Gly
         1               5                  10                 15

Ser Leu Arg Leu Ser Cys Ala Ala Ser Gly Phe Thr Ile Asp Ser Phe
                         20                  25                 30

Gly Ile His Trp Val Arg Gln Ala Pro Gly Lys Gly Leu Glu Trp Val
                         35                  40                 45

Ala Phe Ile Gly Pro Phe Gly Gly Ser Thr Phe Tyr Ala Asp Ser Val
                 50                  55                 60

Lys Gly Arg Phe Thr Ile Ser Ala Asp Thr Ser Lys Asn Thr Ala Tyr
         65                      70                  75                 80

Leu Gln Met Asn Ser Leu Arg Ala Glu Asp Thr Ala Val Tyr Tyr Cys
                         85                  90                 95

Ala Arg Phe Asp Ser Asn Ser Tyr Ser Tyr His Gly Ile Met Asp Tyr
                         100                 105                110

Trp Gly Gln Gly Thr Leu Val Thr Val Ser Ser
                 115                 120

<210> SEQ ID NO 31
<211> LENGTH: 117
<212> TYPE: PRT
<213> ORGANISM: Artificial Sequence
<220> FEATURE:
<223> OTHER INFORMATION: synthesized-P04_VH

<400> SEQUENCE: 31

Glu Val Gln Leu Val Glu Ser Gly Gly Gly Leu Val Gln Pro Gly Gly
         1               5                  10                 15

Ser Leu Arg Leu Ser Cys Ala Ala Ser Gly Phe Thr Ile Asn Ser Trp
                         20                  25                 30

Ser Ile His Trp Val Arg Gln Ala Pro Gly Lys Gly Leu Glu Trp Val
                         35                  40                 45

Ala Ser Ile Trp Pro Phe Gly Gly Phe Thr Phe Tyr Ala Asp Ser Val
                 50                  55                 60
```

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Ser Phe Gly Asp Tyr Trp Gly Gln Gly Thr Leu
            100                 105                 110

Val Thr Val Ser Ser
        115

<210> SEQ ID NO 32
<211> LENGTH: 121
<212> TYPE: PRT
<213> ORGANISM: Artificial Sequence
<220> FEATURE:
<223> OTHER INFORMATION: synthesized-P05_VH

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asp Tyr
            20                  25                  30

Gly Ile His Trp Val Arg Gln Ala Pro Gly Lys Gly Leu Glu Trp Val
        35                  40                  45

Ala Gly Ile Trp Pro Tyr Trp Gly Phe Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe His Gly Ser Ser Tyr Tyr Ser Val Met Asp Tyr Trp Gly
            100                 105                 110

Gln Gly Thr Leu Val Thr Val Ser Ser
        115                 120

<210> SEQ ID NO 33
<211> LENGTH: 120
<212> TYPE: PRT
<213> ORGANISM: Artificial Sequence
<220> FEATURE:
<223> OTHER INFORMATION: synthesized-P06_VH

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Gly Tyr
            20                  25                  30

Trp Ile His Trp Val Arg Gln Ala Pro Gly Lys Gly Leu Glu Trp Val
        35                  40                  45

Ala Gly Ile Gly Pro Tyr Trp Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asn Asn Trp Phe Trp Asn Val Met Asp Tyr Trp Gly Gln
            100                 105                 110

Gly Thr Leu Val Thr Val Ser Ser
        115                 120

<210> SEQ ID NO 34
<211> LENGTH: 120
<212> TYPE: PRT
<213> ORGANISM: Artificial Sequence
<220> FEATURE:
<223> OTHER INFORMATION: synthesized-P10_VH

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asp Asn Ser
            20                  25                  30

Trp Ile His Trp Val Arg Gln Ala Pro Gly Lys Gly Leu Glu Trp Val
        35                  40                  45

Ala Ser Ile Trp Pro Phe Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Asn Val Phe Asp Trp Tyr Met Asp Tyr Trp Gly Gln
            100                 105                 110

Gly Thr Leu Val Thr Val Ser Ser
        115                 120
```

<210> SEQ ID NO 35
<211> LENGTH: 120
<212> TYPE: PRT
<213> ORGANISM: Artificial Sequence
<220> FEATURE:
<223> OTHER INFORMATION: synthesized-P11_VH

<400> SEQUENCE: 35

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Phe
            20                  25                  30

Trp Ile His Trp Val Arg Gln Ala Pro Gly Lys Gly Leu Glu Trp Val
        35                  40                  45

Ala Gly Ile Gly Pro Phe Trp Gly Ser Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asn Asp Trp Phe Tyr His Gly Met Asp Tyr Trp Gly Gln
            100                 105                 110

Gly Thr Leu Val Thr Val Ser Ser
        115                 120
```

<210> SEQ ID NO 36
<211> LENGTH: 120
<212> TYPE: PRT
<213> ORGANISM: Artificial Sequence
<220> FEATURE:
<223> OTHER INFORMATION: synthesized-P12_VH

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Asp Tyr
            20                  25                  30

Tyr Ile His Trp Val Arg Gln Ala Pro Gly Lys Gly Leu Glu Trp Val
        35                  40                  45

Ala Gly Ile Gly Pro Ser Trp Gly Ser Thr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Phe Tyr Asn Asn His Trp Gly Phe Met Asp Tyr Trp Gly Gln
            100                 105                 110

Gly Thr Leu Val Thr Val Ser Ser
            115                 120

<210> SEQ ID NO 37
<211> LENGTH: 120
<212> TYPE: PRT
<213> ORGANISM: Artificial Sequence
<220> FEATURE:
<223> OTHER INFORMATION: synthesized-P14_VH

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Asp Phe
            20                  25                  30

Gly Ile His Trp Val Arg Gln Ala Pro Gly Lys Gly Leu Glu Trp Val
        35                  40                  45

Ala Gly Ile Trp Pro Phe Gly Gly Tyr Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Phe Val Asn Trp Asp Gly Asp Tyr Met Asp Tyr Trp Gly Gln
            100                 105                 110

Gly Thr Leu Val Thr Val Ser Ser
            115                 120

<210> SEQ ID NO 38
<211> LENGTH: 119
<212> TYPE: PRT
<213> ORGANISM: Artificial Sequence
<220> FEATURE:
<223> OTHER INFORMATION: synthesized-P25_VH

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asn Gly
            20                  25                  30

Gly Ile His Trp Val Arg Gln Ala Pro Gly Lys Gly Leu Glu Trp Val
        35                  40                  45

Ala Gly Ile Gly Pro Tyr Gly Gly Tyr Thr Tyr Tyr Ala Asp Ser Val
50                  55                  60

```
Lys Gly Arg Phe Thr Ile Ser Ala Asp Thr Ser Lys Asn Thr Ala Tyr
65                  70                  75                  80

Leu Gln Thr Asn Ser Leu Arg Ala Glu Asp Thr Ala Val Tyr Tyr Cys
                85                  90                  95

Ala Arg Phe Tyr Gly Tyr Ser Gly Ile Met Asp Tyr Trp Gly Gln Gly
            100                 105                 110

Thr Leu Val Thr Val Ser Ser
        115
```

<210> SEQ ID NO 39
<211> LENGTH: 120
<212> TYPE: PRT
<213> ORGANISM: Artificial Sequence
<220> FEATURE:
<223> OTHER INFORMATION: synthesized-P26_VH

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asp Asn Ser
            20                  25                  30

Trp Ile His Trp Val Arg Gln Ala Pro Gly Lys Gly Leu Glu Trp Val
        35                  40                  45

Ala Ser Ile Gly Pro Tyr Trp Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Leu Pro Tyr Ala Met Asp Tyr Trp Gly Gln
            100                 105                 110

Gly Thr Leu Val Thr Val Ser Ser
        115                 120
```

<210> SEQ ID NO 40
<211> LENGTH: 121
<212> TYPE: PRT
<213> ORGANISM: Artificial Sequence
<220> FEATURE:
<223> OTHER INFORMATION: synthesized-P28_VH

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asn Ser
            20                  25                  30

Gly Ile His Trp Val Arg Gln Ala Pro Gly Lys Gly Leu Glu Trp Val
        35                  40                  45

Ala Ser Ile Trp Pro Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asn Ser Ser Tyr Ser Ser Gly Leu Met Asp Tyr Trp Gly
            100                 105                 110

Gln Gly Thr Leu Val Thr Val Ser Ser
```

115           120

<210> SEQ ID NO 41
<211> LENGTH: 121
<212> TYPE: PRT
<213> ORGANISM: Artificial Sequence
<220> FEATURE:
<223> OTHER INFORMATION: synthesized-P37_VH

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Trp
            20                  25                  30

Gly Ile His Trp Val Arg Gln Ala Pro Gly Lys Gly Leu Glu Trp Val
        35                  40                  45

Ala Gly Ile Trp Pro Tyr Trp Gly Phe Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe His Gly Ser Ser Tyr Tyr Ser Val Met Asp Tyr Trp Gly
            100                 105                 110

Gln Gly Thr Leu Val Thr Val Ser Ser
        115                 120

<210> SEQ ID NO 42
<211> LENGTH: 123
<212> TYPE: PRT
<213> ORGANISM: Artificial Sequence
<220> FEATURE:
<223> OTHER INFORMATION: synthesized-P38_VH

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asp Gly
            20                  25                  30

Gly Ile His Trp Val Arg Gln Ala Pro Gly Lys Gly Leu Glu Trp Val
        35                  40                  45

Ala Phe Ile Gly Pro Tyr Gly Gly Ser Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Phe Ile Gly Asp Tyr Ser Ser Tyr His Gly Val Met Asp Tyr
            100                 105                 110

Trp Gly Gln Gly Thr Leu Val Thr Val Ser Ser
        115                 120

<210> SEQ ID NO 43
<211> LENGTH: 118
<212> TYPE: PRT
<213> ORGANISM: Artificial Sequence
<220> FEATURE:
<223> OTHER INFORMATION: synthesized-P44_VH

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asp Gly Trp
            20                  25                  30

Trp Ile His Trp Val Arg Gln Ala Pro Gly Lys Gly Leu Glu Trp Val
        35                  40                  45

Ala Gly Ile Trp Pro Phe Gly Gly Phe Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Tyr Ser Gly Tyr Ser Gly Asp Tyr Trp Gly Gln Gly Thr
            100                 105                 110

Leu Val Thr Val Ser Ser
        115
```

<210> SEQ ID NO 44
<211> LENGTH: 120
<212> TYPE: PRT
<213> ORGANISM: Artificial Sequence
<220> FEATURE:
<223> OTHER INFORMATION: synthesized-P47_VH

<400> SEQUENCE: 44

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Asn Ser
            20                  25                  30

Gly Ile His Trp Val Arg Gln Ala Pro Gly Lys Gly Leu Glu Trp Val
        35                  40                  45

Ala Ser Ile Trp Pro Ser Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly His Ile Asp Gly Asp Ile Met Asp Tyr Trp Gly Gln
            100                 105                 110

Gly Thr Leu Val Thr Val Ser Ser
        115                 120
```

<210> SEQ ID NO 45
<211> LENGTH: 120
<212> TYPE: PRT
<213> ORGANISM: Artificial Sequence
<220> FEATURE:
<223> OTHER INFORMATION: synthesized-P48_VH

<400> SEQUENCE: 45

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Ser Trp
            20                  25                  30

Gly Ile His Trp Val Arg Gln Ala Pro Gly Lys Gly Leu Glu Trp Val
        35                  40                  45

Ala Gly Ile Gly Pro Ser Trp Gly Tyr Thr Ser Tyr Ala Asp Ser Val
```

```
                50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                    85                  90                  95

Ala Arg Phe Gly Asp Gly Asp Phe Asp Leu Met Asp Tyr Trp Gly Gln
                100                 105                 110

Gly Thr Leu Val Thr Val Ser Ser
            115                 120

<210> SEQ ID NO 46
<211> LENGTH: 121
<212> TYPE: PRT
<213> ORGANISM: Artificial Sequence
<220> FEATURE:
<223> OTHER INFORMATION: synthesized-P58_VH

<400> SEQUENCE: 46

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Gly Gly Gly
                20                  25                  30

Gly Ile His Trp Val Arg Gln Ala Pro Gly Lys Gly Leu Glu Trp Val
            35                  40                  45

Ala Trp Ile Trp Pro Tyr Trp Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                    85                  90                  95

Ala Arg Phe Asn Ser Tyr Ser Tyr Ser Gly Val Met Asp Tyr Trp Gly
                100                 105                 110

Gln Gly Thr Leu Val Thr Val Ser Ser
            115                 120

<210> SEQ ID NO 47
<211> LENGTH: 120
<212> TYPE: PRT
<213> ORGANISM: Artificial Sequence
<220> FEATURE:
<223> OTHER INFORMATION: synthesized-S01_VH

<400> SEQUENCE: 47

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Asn Asn Tyr
                20                  25                  30

Gly Ile His Trp Val Arg Gln Ala Pro Gly Lys Gly Leu Glu Trp Val
            35                  40                  45

Ala Ser Ile Trp Pro Ser Gly Gly Tyr Thr Ser Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                    85                  90                  95

Ala Arg Phe Gly Leu Gly Asp Tyr Asp Ile Met Asp Tyr Trp Gly Gln
                100                 105                 110
```

```
Gly Thr Leu Val Thr Val Ser Ser
        115                 120

<210> SEQ ID NO 48
<211> LENGTH: 120
<212> TYPE: PRT
<213> ORGANISM: Artificial Sequence
<220> FEATURE:
<223> OTHER INFORMATION: synthesized-S06_VH

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Gly Gly
            20                  25                  30

Trp Ile His Trp Val Arg Gln Ala Pro Gly Lys Gly Leu Glu Trp Val
        35                  40                  45

Ala Phe Ile Gly Pro Tyr Gly Gly Ser Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asn Phe Gly Phe Trp Asn His Met Asp Tyr Trp Gly Gln
            100                 105                 110

Gly Thr Leu Val Thr Val Ser Ser
        115                 120

<210> SEQ ID NO 49
<211> LENGTH: 120
<212> TYPE: PRT
<213> ORGANISM: Artificial Sequence
<220> FEATURE:
<223> OTHER INFORMATION: synthesized-S07_VH

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Ser Ser
            20                  25                  30

Gly Ile His Trp Val Arg Gln Ala Pro Gly Lys Gly Leu Glu Trp Val
        35                  40                  45

Ala Ser Ile Gly Pro Ser Trp Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Ile Gly Asp Ile Asp Val Met Asp Tyr Trp Gly Gln
            100                 105                 110

Gly Thr Leu Val Thr Val Ser Ser
        115                 120

<210> SEQ ID NO 50
<211> LENGTH: 120
<212> TYPE: PRT
<213> ORGANISM: Artificial Sequence
<220> FEATURE:
<223> OTHER INFORMATION: synthesized-S10_VH
```

```
<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Gly Tyr
            20                  25                  30

Gly Ile His Trp Val Arg Gln Ala Pro Gly Lys Gly Leu Glu Trp Val
        35                  40                  45

Ala Ser Ile Gly Pro Ser Trp Gly Phe Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asn Trp Val Ile Asn Gly Val Thr Asp Tyr Trp Gly Gln
                100                 105                 110

Gly Thr Leu Val Thr Val Ser Ser
        115                 120

<210> SEQ ID NO 51
<211> LENGTH: 120
<212> TYPE: PRT
<213> ORGANISM: Artificial Sequence
<220> FEATURE:
<223> OTHER INFORMATION: synthesized-S11_VH

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asp Asn Gly
            20                  25                  30

Gly Ile His Trp Val Arg Gln Ala Pro Gly Lys Gly Leu Glu Trp Val
        35                  40                  45

Ala Trp Ile Gly Pro Tyr Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Phe Gly Leu His Asp Leu Met Asp Tyr Trp Gly Gln
                100                 105                 110

Gly Thr Leu Val Thr Val Ser Ser
        115                 120

<210> SEQ ID NO 52
<211> LENGTH: 120
<212> TYPE: PRT
<213> ORGANISM: Artificial Sequence
<220> FEATURE:
<223> OTHER INFORMATION: synthesized-S29_VH

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45
```

```
Ala Ser Ile Trp Pro Ser Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
 65                 70                  75                  80

Leu Gln Met Asn Ser Leu Arg Ala Glu Asp Thr Ala Val Tyr Tyr Cys
                 85                  90                  95

Ala Arg Phe Asn Trp Ile Val Gly His Tyr Met Asp Tyr Trp Gly Gln
                100                 105                 110

Gly Thr Leu Val Thr Val Ser Ser
            115                 120

<210> SEQ ID NO 53
<211> LENGTH: 120
<212> TYPE: PRT
<213> ORGANISM: Artificial Sequence
<220> FEATURE:
<223> OTHER INFORMATION: synthesized-S40_VH

<400> SEQUENCE: 53

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Ile Gly Asp Phe
                 20                  25                  30

Gly Ile His Trp Val Arg Gln Ala Pro Gly Lys Gly Leu Glu Trp Val
             35                  40                  45

Ala Gly Ile Trp Pro Phe Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
 65                 70                  75                  80

Leu Gln Met Asn Ser Leu Arg Ala Glu Asp Thr Ala Val Tyr Tyr Cys
                 85                  90                  95

Ala Arg Phe Val Asn Trp Asp Gly Asp Tyr Met Asp Tyr Trp Gly Gln
                100                 105                 110

Gly Thr Leu Val Thr Val Ser Ser
            115                 120

<210> SEQ ID NO 54
<211> LENGTH: 120
<212> TYPE: PRT
<213> ORGANISM: Artificial Sequence
<220> FEATURE:
<223> OTHER INFORMATION: synthesized-S45_VH

<400> SEQUENCE: 54

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Ile Asn Gly Ser
                 20                  25                  30

Ser Ile His Trp Val Arg Gln Ala Pro Gly Lys Gly Leu Glu Trp Val
             35                  40                  45

Ala Tyr Ile Gly Pro Phe Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
 65                 70                  75                  80

Leu Gln Met Asn Ser Leu Arg Ala Glu Asp Thr Ala Val Tyr Tyr Cys
                 85                  90                  95

Ala Arg Phe Trp His Gly Tyr Asn Leu Tyr Met Asp Tyr Trp Gly Gln
                100                 105                 110
```

```
Gly Thr Leu Val Thr Val Ser Ser
        115                 120

<210> SEQ ID NO 55
<211> LENGTH: 120
<212> TYPE: PRT
<213> ORGANISM: Artificial Sequence
<220> FEATURE:
<223> OTHER INFORMATION: synthesized-S48_VH

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Ile Gly Asp Gly
            20                  25                  30

Ser Ile His Trp Val Arg Gln Ala Pro Gly Lys Gly Leu Glu Trp Val
        35                  40                  45

Ala Ser Ile Gly Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe His Tyr Gly Tyr Trp Asn Asn Met Asp Tyr Trp Gly Gln
            100                 105                 110

Gly Thr Leu Val Thr Val Ser Ser
        115                 120

<210> SEQ ID NO 56
<211> LENGTH: 120
<212> TYPE: PRT
<213> ORGANISM: Artificial Sequence
<220> FEATURE:
<223> OTHER INFORMATION: synthesized-S51_VH

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asp Asp Trp
            20                  25                  30

Gly Ile His Trp Val Arg Gln Ala Pro Gly Lys Gly Leu Glu Trp Val
        35                  40                  45

Ala Trp Ile Trp Pro Tyr Gly Gly Phe Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Phe Val Asp Trp Asn Leu Met Asp Tyr Trp Gly Gln
            100                 105                 110

Gly Thr Leu Val Thr Val Ser Ser
        115                 120

<210> SEQ ID NO 57
<211> LENGTH: 36
<212> TYPE: DNA
<213> ORGANISM: Artificial Sequence
<220> FEATURE:
<223> OTHER INFORMATION: CDR-H_F primer
```

```
<400> SEQUENCE: 57
cgtgtcgcat ctgaagtgca gctggtggaa tcggga                              36

<210> SEQ ID NO 58
<211> LENGTH: 48
<212> TYPE: DNA
<213> ORGANISM: Artificial Sequence
<220> FEATURE:
<223> OTHER INFORMATION: CDR-H_R primer

<400> SEQUENCE: 58
gaccgatggg cccttggtgc tagccgagct cacggtaaca agggtgcc                 48

<210> SEQ ID NO 59
<211> LENGTH: 59
<212> TYPE: DNA
<213> ORGANISM: Artificial Sequence
<220> FEATURE:
<223> OTHER INFORMATION: CDR-L_F primer

<400> SEQUENCE: 59
caggtgcacg atgtgatggt accgatattc aaatgaccca gagcccgagc agcctgagc     59

<210> SEQ ID NO 60
<211> LENGTH: 36
<212> TYPE: DNA
<213> ORGANISM: Artificial Sequence
<220> FEATURE:
<223> OTHER INFORMATION: CDR-L_R primer

<400> SEQUENCE: 60
tgcagccacc gtacgtttga tttccacctt ggtgcc                              36

<210> SEQ ID NO 61
<211> LENGTH: 38
<212> TYPE: PRT
<213> ORGANISM: Artificial Sequence
<220> FEATURE:
<223> OTHER INFORMATION: synthesized-signal peptide

<400> SEQUENCE: 61

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala
        35

<210> SEQ ID NO 62
<211> LENGTH: 45
<212> TYPE: PRT
<213> ORGANISM: Artificial Sequence
<220> FEATURE:
<223> OTHER INFORMATION: synthesized-thrombin cutting site

<400> SEQUENCE: 62

Ala Ser Leu Val Pro Arg Gly Ser Pro Gly Ser Gly Tyr Ile Pro Glu
1               5                   10                  15

Ala Pro Arg Asp Gly Gln Ala Tyr Val Arg Lys Asp Gly Glu Trp Val
            20                  25                  30

Leu Leu Ser Thr Phe Leu Gly His His His His His
        35                  40                  45
```

-continued

<210> SEQ ID NO 63
<211> LENGTH: 113
<212> TYPE: PRT
<213> ORGANISM: Artificial Sequence
<220> FEATURE:
<223> OTHER INFORMATION: synthesized_F10-VL

<400> SEQUENCE: 63

```
Ile Gln Pro Gly Leu Thr Gln Pro Pro Ser Val Ser Lys Gly Leu Arg
1               5                   10                  15

Gln Thr Ala Thr Leu Thr Cys Thr Gly Asn Ser Asn Asn Val Gly Asn
            20                  25                  30

Gln Gly Ala Ala Trp Leu Gln His Gln Gly His Pro Pro Lys Leu
        35                  40                  45

Leu Ser Tyr Arg Asn Asn Asp Arg Pro Ser Gly Ile Ser Glu Arg Phe
    50                  55                  60

Ser Ala Ser Arg Ser Gly Asn Thr Ala Ser Leu Thr Ile Thr Gly Leu
65                  70                  75                  80

Gln Pro Glu Asp Glu Ala Asp Tyr Tyr Cys Ser Thr Trp Asp Ser Ser
                85                  90                  95

Leu Ser Ala Val Val Phe Gly Gly Thr Lys Leu Thr Val Leu Gly
            100                 105                 110

Thr
```

<210> SEQ ID NO 64
<211> LENGTH: 125
<212> TYPE: PRT
<213> ORGANISM: Artificial Sequence
<220> FEATURE:
<223> OTHER INFORMATION: synthesized_F10-VH

<400> SEQUENCE: 64

```
Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ala Ser
        115                 120                 125
```

<210> SEQ ID NO 65
<211> LENGTH: 112
<212> TYPE: PRT
<213> ORGANISM: Artificial Sequence
<220> FEATURE:
<223> OTHER INFORMATION: synthesized_FI6V3-VL

<400> SEQUENCE: 65

```
Asp Ile Val Met Thr Gln Ser Pro Asp Ser Leu Ala Val Ser Leu Gly
1               5                   10                  15
```

Glu Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys Arg
            100                 105                 110

<210> SEQ ID NO 66
<211> LENGTH: 129
<212> TYPE: PRT
<213> ORGANISM: Artificial Sequence
<220> FEATURE:
<223> OTHER INFORMATION: synthesized_FI6V3-VH

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 67
<211> LENGTH: 108
<212> TYPE: PRT
<213> ORGANISM: Artificial Sequence
<220> FEATURE:
<223> OTHER INFORMATION: synthesized_C05-VL

<400> SEQUENCE: 67

Asp Ile Gln Leu Thr Gln Ser Pro Ser Ser Leu Ser Ala Ser Val Gly
1               5                   10                  15

Asp Arg Val Thr Leu Thr Cys Gln Ala Ser Gln Asp Ile Arg Lys Phe
            20                  25                  30

Leu Asn Trp Tyr Gln Gln Lys Pro Gly Lys Pro Lys Leu Leu Ile
        35                  40                  45

Tyr Asp Ala Ser Asn Leu Gln Arg Gly Val Pro Ser Arg Phe Ser Gly
 50                  55                  60

Gly Gly Ser Gly Thr Asp Phe Thr Leu Ile Ile Ser Ser Leu Gln Pro
65                  70                  75                  80

```
Glu Asp Val Gly Thr Tyr Tyr Cys Gln Gln Tyr Asp Gly Leu Pro Phe
                85                  90                  95

Thr Phe Gly Gly Gly Thr Lys Val Glu Ile Lys Arg
            100                 105

<210> SEQ ID NO 68
<211> LENGTH: 138
<212> TYPE: PRT
<213> ORGANISM: Artificial Sequence
<220> FEATURE:
<223> OTHER INFORMATION: synthesized_C05-VH

<400> SEQUENCE: 68

Pro Val Gln Leu Gln Glu Ser Gly Gly Gly Leu Val Gln Pro Gly Glu
1               5                   10                  15

Ser Leu Arg Leu Ser Cys Val Ser Gly Ser Ser Phe Gly Glu Ser
            20                  25                  30

Thr Leu Ser Tyr Tyr Ala Val Ser Trp Val Arg Gln Ala Pro Gly Lys
        35                  40                  45

Gly Leu Glu Trp Leu Ser Ile Ile Asn Ala Gly Gly Asp Ile Asp
    50                  55                  60

Tyr Ala Asp Ser Val Glu Gly Arg Phe Thr Ile Ser Arg Asp Asn Ser
65                  70                  75                  80

Lys Glu Thr Leu Tyr Leu Gln Met Thr Asn Leu Arg Val Glu Asp Thr
                85                  90                  95

Gly Val Tyr Tyr Cys Ala Lys His Met Ser Met Gln Gln Val Val Ser
            100                 105                 110

Ala Gly Trp Glu Arg Ala Asp Leu Val Gly Asp Ala Phe Asp Val Trp
        115                 120                 125

Gly Gln Gly Thr Met Val Thr Val Ser Ser
    130                 135

<210> SEQ ID NO 69
<211> LENGTH: 110
<212> TYPE: PRT
<213> ORGANISM: Artificial Sequence
<220> FEATURE:
<223> OTHER INFORMATION: synthesized_CR8020-VL

<400> SEQUENCE: 69

Gln Glu Ile Val Met Thr Gln Ser Pro Gly Thr Leu Ser Leu Ser Pro
1               5                   10                  15

Gly Glu Arg Ala Thr Leu Ser Cys Arg Ala Ser Gln Ser Val Ser Met
            20                  25                  30

Asn Tyr Leu Ala Trp Phe Gln Gln Lys Pro Gly Gln Ala Pro Arg Leu
        35                  40                  45

Leu Ile Tyr Gly Ala Ser Arg Arg Ala Thr Gly Ile Pro Asp Arg Ile
    50                  55                  60

Ser Gly Ser Gly Ser Gly Thr Asp Phe Thr Leu Thr Ile Ser Arg Leu
65                  70                  75                  80

Glu Pro Ala Asp Phe Ala Val Tyr Tyr Cys Gln Gln Tyr Gly Thr Ser
                85                  90                  95

Pro Arg Thr Phe Gly Gln Gly Ala Lys Val Glu Ile Lys Arg
            100                 105                 110

<210> SEQ ID NO 70
<211> LENGTH: 122
<212> TYPE: PRT
```

-continued

```
<213> ORGANISM: Artificial Sequence
<220> FEATURE:
<223> OTHER INFORMATION: synthesized_CR8020-VH

<400> SEQUENCE: 70

Glu Val Gln Leu Gln Gln Ser Gly Ala Glu Val Lys Thr Pro Gly Ala
1               5                   10                  15

Ser Val Lys Val Ser Cys Lys Ala Ser Gly Tyr Thr Phe Thr Ser Phe
            20                  25                  30

Gly Val Ser Trp Ile Arg Gln Ala Pro Gly Gln Gly Leu Glu Trp Ile
        35                  40                  45

Gly Trp Ile Ser Ala Tyr Asn Gly Asp Thr Tyr Ala Gln Lys Phe
    50                  55                  60

Gln Ala Arg Val Thr Met Thr Thr Asp Thr Ser Thr Thr Thr Ala Tyr
65                  70                  75                  80

Met Glu Met Arg Ser Leu Arg Ser Asp Asp Thr Ala Val Tyr Tyr Cys
                85                  90                  95

Ala Arg Glu Pro Pro Leu Phe Tyr Ser Ser Trp Ser Leu Asp Asn Trp
            100                 105                 110

Gly Gln Gly Thr Leu Val Thr Val Ser Ser
        115                 120

<210> SEQ ID NO 71
<211> LENGTH: 108
<212> TYPE: PRT
<213> ORGANISM: Artificial Sequence
<220> FEATURE:
<223> OTHER INFORMATION: synthesized_Do1-VL

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Gly
            20                  25                  30

Val Ala Trp Tyr Gln Gln Lys Pro Gly Lys Ala Pro Lys Leu Leu Ile
        35                  40                  45

Phe Phe Ser Arg Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Gly Pro Leu
                85                  90                  95

Thr Phe Gly Gln Gly Thr Lys Val Glu Ile Lys Arg
            100                 105

<210> SEQ ID NO 72
<211> LENGTH: 121
<212> TYPE: PRT
<213> ORGANISM: Artificial Sequence
<220> FEATURE:
<223> OTHER INFORMATION: synthesized_Do1-VH

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asp Asn Gly
            20                  25                  30

Ser Ile His Trp Val Arg Gln Ala Pro Gly Lys Gly Leu Glu Trp Val
        35                  40                  45
```

-continued

```
Ala Trp Ile Gly Pro Tyr Gly Gly Phe Thr Ser Tyr Ala Asp Ser Val
    50              55              60

Lys Gly Arg Phe Thr Ile Ser Ala Asp Thr Ser Lys Asn Thr Ala Tyr
65              70              75              80

Leu Gln Met Asn Ser Leu Arg Ala Glu Asp Thr Ala Val Tyr Tyr Cys
            85              90              95

Ala Arg Phe Tyr Gly Ser Gly Ser Ser Ser Phe Met Asp Tyr Trp Gly
            100             105             110

Gln Gly Thr Leu Val Thr Val Ser Ser
        115             120
```